United States Patent
Hu et al.

(10) Patent No.: US 11,075,008 B2
(45) Date of Patent: Jul. 27, 2021

(54) GENERATING DRUG REPOSITIONING HYPOTHESES BASED ON INTEGRATING MULTIPLE ASPECTS OF DRUG SIMILARITY AND DISEASE SIMILARITY

(71) Applicant: International Business Machines Corporation, Armonk, NY (US)

(72) Inventors: Jianying Hu, Bronx, NY (US); Fei Wang, Briarcliff Manor, NY (US); Ping Zhang, White Plains, NY (US)

(73) Assignee: International Business Machines Corporation, Armonk, NY (US)

( * ) Notice: Subject to any disclaimer, the term of this patent is extended or adjusted under 35 U.S.C. 154(b) by 397 days.

(21) Appl. No.: 14/749,700

(22) Filed: Jun. 25, 2015

(65) Prior Publication Data

US 2016/0140312 A1 May 19, 2016

Related U.S. Application Data

(63) Continuation of application No. 14/541,285, filed on Nov. 14, 2014.

(51) Int. Cl.
*G16H 50/50* (2018.01)
*G16C 20/40* (2019.01)
(Continued)

(52) U.S. Cl.
CPC ............. *G16H 50/50* (2018.01); *G16C 20/30* (2019.02); *G16C 20/40* (2019.02); *G16C 20/50* (2019.02)

(58) Field of Classification Search
CPC .. G06F 19/704; G06F 19/3437; G06F 19/705; G06F 19/706; G06F 19/00; C07D 305/14; G16C 20/30; G16C 20/40
(Continued)

(56) References Cited

U.S. PATENT DOCUMENTS

2010/0234236 A1 9/2010 Cohen et al.
2012/0184560 A1 7/2012 Wong et al.
(Continued)

FOREIGN PATENT DOCUMENTS

| EP | 2065821 | 6/2009 |
|---|---|---|
| WO | 2009068659 | 6/2009 |
| WO | 2013028480 | 2/2013 |

OTHER PUBLICATIONS

English machine translation of Korean Patent KR 101450784 Jung et al. Jul. 2, 2013.*
(Continued)

*Primary Examiner* — Thinh T Nguyen
(74) *Attorney, Agent, or Firm* — Fleit Intellectual Property Law; Thomas S. Grzesik

(57) ABSTRACT

Various embodiments predict drug-disease associations. In one embodiment, a plurality of disease similarity matrices and a plurality of disease similarity matrices are accessed. Each of the plurality of drug similarity matrices is associated with a different drug information source. Each of the plurality of disease similarity matrices is associated with a different disease information source. A known drug-disease association matrix is also accessed. The known drug-disease association matrix indicates if a given drug identified is known to treat a given disease. At least one drug-disease association prediction is generated based on the plurality of drug similarity matrices, the plurality of disease similarity matrices, and the known drug-disease association matrix. The at least one drug-disease association prediction identifies a previously unknown association between a given drug and a given disease, and a probability that the given disease is treatable by the given drug.

11 Claims, 24 Drawing Sheets

(51) Int. Cl.
G16C 20/30 (2019.01)
G16C 20/50 (2019.01)
(58) Field of Classification Search
USPC ..................................... 702/19, 30, 119, 20
See application file for complete search history.

(56) References Cited

U.S. PATENT DOCUMENTS

| | | | | |
|---|---|---|---|---|
| 2012/0296090 | A1* | 11/2012 | Wong et al. | G16H 50/50 544/119 |
| 2013/0217707 | A1 | 8/2013 | Faraone | |
| 2014/0193517 | A1 | 7/2014 | Agarwal et al. | |
| 2014/0274764 | A1* | 9/2014 | Zhu | C12Q 1/6883 506/9 |
| 2015/0227700 | A1* | 8/2015 | Bundela et al. | G06F 17/3053 707/730 |
| 2015/0292014 | A1* | 10/2015 | Zhu | C12Q 1/6883 506/2 |
| 2015/0324546 | A1* | 11/2015 | Dakshanamurthy et al. | G06F 19/3456 705/2 |

OTHER PUBLICATIONS

Li, H., et al., "Drug Design Targeting Protein-Protein Interactions (PPI) Using Multiple Ligand Simultaneous Docking (MLSD) and Drug Repositioning: Discovery of Raloxifene and Bazedoxifene as Novel Inhibitors of IL-6/GP130 Interface", Journal of Medicinal Chemistry, Downloaded from http://pubs.acs.org on Jan. 23, 2014, pp. 1-35.

Quabaja, A. et al., "Prediction of novel drug indications using network driven biological data prioritization and integration", Journal of Cheminformatics, Published on Jan. 7, 2014, pp. 1-14, vol. 6, Issue 1.

Chiang, A. et al., "Systematic Evaluation of Drug-Disease Relationships to Identify Leads for Novel Drug Uses," Clinical Pharmacology and Therapeutics, Nov. 2009, 86(5): pp. 1-8.

Luo, H. et al., "DRAR-CPI: a server for identifying drug repositioning potential and adverse drug reactions via the chemical-protein interactome", Nucleic Acid Research, May 10, 2011, pp. 1-7, vol. 39.

Wang, K. et al., "Prediction of Drug-Target Interactions for Drug Repositioning Only Based on Genomic Expression Similarity", PLOS Computational Biology, Nov. 7, 2013, pp. 1-9, vol. 9, Issue 11.

Gottlieb, A. et al., "PREDICT: a method for inferring novel drug indications with application to personalized medicine", Molecular Systems Biology, Dec. 4, 2011, pp. 1-9, vol. 7, Article 496.

Zhang, P. et al., "Computational Drug Repositioning by Ranking and Integrating Multiple Data Sources", Proceedings of the European Conference on Machine Learning and Principles and Practice of Knowledge Discovery in Databases, Sep. 23-27, 2013, pp. 579-594.

Wang, Y. et al., "Drug Repositioning by Kernel-Based Integration of Molecular Structure, Molecular Activity, and Phenotype Data", PLOS One, Nov. 11, 2013, pp. 1-12., vol. 8, Issue 11.

Sanseau, P. et al., "Use of genome-wide association studies for drug repositioning," Nature Biotechnology, Apr. 2012, pp. 317-320, vol. 30, No. 4.

Yang, L. et al., "Systematic Drug Repositioning Based on Clinical Side-Effects" PLOS One, Dec. 21, 2011, pp. 1-9, vol. 6, Issue 12.

Hurle, M. et al., "Computational Drug Repositioning: From Data to Therapeutics", Clinical Pharmacology and Therapeutics, Apr. 2013, pp. 335-341,vol. 93, No. 4.

Sardana, D. et al., "Drug Repositioning for Orphan diseases", Briefings in Bioinformatics, Apr. 18, 2011, pp. 346-356, vol. 12, No. 4.

Hu, G., et al., "Human Disease-Drug Network Based on Genomic Expression Profiles," PLOS One, Aug. 2009, pp. 1-11, vol. 4, Issue 8.

Dakshanamurthy, S. et al., "Predicting New Indications for Approved Drugs Using a Proteo-Chemometric Method", Journal of Medicinal Chemistry, Aug. 9, 2012, pp. 1-34, vol. 55, Issue 15.

Cheng, F. et al., "Prediction of chemical-protein interactions: multitarget-QSAR versus computational chemogenomic methods", Molecular Biosystems, May 2012, pp. 2373-2384.

Li, J., et al., "Pathway-based drug repositioning using causal inference", Asia Pacific Bioinformatics Network (APBioNet) Twelfth International Conference on Bioinformatics (InCoB2013), Sep. 20-22, 2013, pp. 1-10.

Iorio, F. et al., " Discovery of drug mode of action and drug repositioning from transcriptional responses", Proceedings of the National Academy of Sciences of the United States of America, Aug. 17, 2010, pp. 14621-14626, vol. 10, No. 33.

Campillos, M., "Drug Target Identification Using Side-Effect Similarity", www.sciencemag.org, Jul. 11, 2008, pp. 263-266, vol. 321.

Ye, H., et al. " Construction of Drug Network Based on Side Effects and Its Application for Drug Repositioning," PLOS One, Feb. 2014, pp. 1-10, vol. 9, Issue 2.

Sirota, M., et al., "Discovery and preclinical validation of drug indications using compendia of public gene expression data", Science Translational Medicine, Aug. 17, 2011, pp. 1-22, vol. 3, Issue 6.

Li, J., et al., "A New Method for Computational Drug Repositioning Using Drug Pairwise Similarity", Proceedings of the IEEE International Conference on Bioinformatics and Biomedicine, Oct. 4-7, 2012, pp. 1-4.

Huang, Y. et al., " Inferring drug-disease associations from integration of chemical, genomic and phenotype data using network propagation", Proceedings of the IEEE International Conference on Bioinformatics and Biomedicine, Oct. 4-7, 2012, pp. 1-14.

Napolitano, F., et al., " Drug repositioning: a machine-learning approach through data integration", Journal of Cheminformatics, Jun. 22, 2013, pp. 1-9.

Dudley, J. et al., "Exploiting drug-disease relationships for computational drug repositioning", Briefings in Bioinformatics, Jun. 20, 2011, pp. 303-311, vol. 23, No. 4.

Duran-Frigola, M. et al., "Recycling side-effects into clinical markers for drug repositioning", Genome Medicine, Jan. 27, 2012, pp. 1-4, vol. 4, Issue 3.

Bertsekas, D., "On the Goldstein-Levitin-Polyak Gradient Projection Method," IEEE Transactions on Automatic Control, Apr. 1976, pp. 174-184, vol. 21, No. 02.

Chen, Y., et al., "Projection Onto a Simplex," Feb. 9, 2011, pp. 1-7.

Lin, C., "Projected Gradient Methods for Non-negative matrix factorization," Neural Computation, Oct. 2007, pp. 1 -27, vol. 19, Issue 10.

Wang, F., et al., "Community Discovery Using Non-negative matrix factorization," Data Min Knowl Disc, Jun. 16, 2010, pp. 1-29.

List of IBM Patents or Applications Treated as Related.

* cited by examiner

|     | $d_1$ | $d_2$ | $d_3$ | $\cdots$ | $d_n$ |
|-----|-------|-------|-------|----------|-------|
| $d_1$ | $D_{11}^{chem}$ | $D_{12}^{chem}$ | $D_{13}^{chem}$ | $\cdots$ | $D_{1n}^{chem}$ |
| $d_2$ | $D_{21}^{chem}$ | $D_{22}^{chem}$ | $D_{23}^{chem}$ | $\cdots$ | $D_{2n}^{chem}$ |
| $d_3$ | $D_{31}^{chem}$ | $D_{32}^{chem}$ | $D_{33}^{chem}$ | $\cdots$ | $D_{3n}^{chem}$ |
| $\vdots$ | $\vdots$ | $\vdots$ | $\vdots$ | $\vdots$ | $\vdots$ |
| $d_n$ | $D_{n1}^{chem}$ | $D_{n2}^{chem}$ | $D_{n3}^{chem}$ | $\cdots$ | $D_{nn}^{chem}$ |

FIG. 2

|       | $d_1$        | $d_2$        | $d_3$        | ... | $d_n$        |
|-------|--------------|--------------|--------------|-----|--------------|
| $d_1$ | $D^{se}_{11}$ | $D^{se}_{12}$ | $D^{se}_{13}$ | ... | $D^{se}_{1n}$ |
| $d_2$ | $D^{se}_{21}$ | $D^{se}_{22}$ | $D^{se}_{23}$ | ... | $D^{se}_{2n}$ |
| $d_3$ | $D^{se}_{31}$ | $D^{se}_{32}$ | $D^{se}_{33}$ | ... | $D^{se}_{3n}$ |
| ...   | ...          | ...          | ...          | ... | ...          |
| $d_n$ | $D^{se}_{n1}$ | $D^{se}_{n2}$ | $D^{se}_{n3}$ | ... | $D^{se}_{nn}$ |

FIG. 4

|  | $s_1$ | $s_2$ | $s_3$ | ... | $s_n$ |
|---|---|---|---|---|---|
| $s_1$ | $S^{pheno}_{11}$ | $S^{pheno}_{12}$ | $S^{pheno}_{13}$ | ... | $S^{pheno}_{1n}$ |
| $s_2$ | $S^{pheno}_{21}$ | $S^{pheno}_{22}$ | $S^{pheno}_{23}$ | ... | $S^{pheno}_{2n}$ |
| $s_3$ | $S^{pheno}_{31}$ | $S^{pheno}_{32}$ | $S^{pheno}_{33}$ | ... | $S^{pheno}_{3n}$ |
| ... | ... | ... | ... | ... | ... |
| $s_n$ | $S^{pheno}_{n1}$ | $S^{pheno}_{n2}$ | $S^{pheno}_{n3}$ | ... | $S^{pheno}_{nn}$ |

FIG. 5

|     | $s_1$ | $s_2$ | $s_3$ | ... | $s_n$ |
|-----|-------|-------|-------|-----|-------|
| $d_1$ | 1 | 0 | 0 | ... | 1 |
| $d_2$ | 1 | 1 | 1 | ... | 1 |
| $d_3$ | 0 | 0 | 1 | ... | 1 |
| ... | ... | ... | ... | ... | ... |
| $d_n$ | 1 | 0 | 1 | ... | 1 |

FIG. 9

Algorithm 1: A BCD Approach for Solving Problem (11)

Require: $\lambda_1 = 0$, $\lambda_2 = 0$, $\delta_1 = 0$, $\delta_2 = 0$, $K_d > 0$, $K_s > 0$, $\{D_k\}_{k=1}^{K_d}$, $\{S_l\}_{l=1}^{K_s}$, $R$ 1: Initialize $\omega = (1/K_d)\mathbf{1} \in \mathbb{R}^{K_d \times 1}$, $\pi = (1/K_s)\mathbf{1} \in \mathbb{R}^{K_s \times 1}$ 2: Initialize $U$ and $V$ by performing Symmetric Nonnegative Matrix Factorization on $\tilde{D} = \sum_{k=1}^{K_d} \omega_k D_k$ and $\tilde{S} = \sum_{l=1}^{K_s} \pi_l S_l$ 3: while Not Converge do

4:     Solve $\Theta$

5:     Solve $\omega$ and $\pi$

6:     Solve $\Lambda$

7:     Solve $U$

8:     Solve $V$

9: end while

FIG. 10

| | $C_{D1}$ | $C_{D2}$ | $C_{D3}$ | ... | $C_{Dn}$ |
|---|---|---|---|---|---|
| $d_1$ | 0.1 | 0.4 | 0.1 | ... | 0.2 |
| $d_2$ | 0.05 | 0.2 | 0.3 | ... | 0.1 |
| $d_3$ | 0.05 | 0.05 | 0.1 | ... | 0.25 |
| ... | ... | ... | ... | ... | ... |
| $d_n$ | 0.5 | 0.02 | 0.1 | ... | 0.05 |

FIG. 11

Require: $0<\beta<1$, $0<\sigma<1$. initialization $A^{(0)}$.

Ensure $A^{(0)} \geq 0$

1: for $k = 1,2,...$ do

2: $\quad A^{(k)} = P_+(A^{(k-1)} - \alpha_k \nabla f(A^{(k-1)}))$, where $\alpha_k = \beta^{t_k}$, and $t_k$ is the first nonnegative integer for which 3: $\quad f(A^{(k)}) - f(A^{(k-1)}) \leq \sigma \nabla f(A^{(k-1)})^T (A^{(k)} - A^{(k-1)})$ 4: end for

FIG. 14

Require: $0<\beta<1$, $0<\sigma<1$. Initialization $A^{(0)}$, $\alpha_0=1$.
Ensure: $A^{(0)} \geq 0$
1: for $k = 1,2,\ldots$ do
2:     Assign $\alpha_k = \alpha_{k-1}$
3:     If $\alpha_k$ satisfies the condition (EQ19)
4:        repeatedly increase it by $\alpha_k \leftarrow \alpha_k/\beta$ until either $\alpha_k$ does not satisfy (EQ19) or $A(\alpha_k/\beta)=A(\alpha_k)$
5:     Else repeatedly decrease $\alpha_k$ by $\alpha_k \leftarrow \alpha_k \cdot \beta$ until $\alpha_k$ satisfies condition (EQ19)
6:     Set $A^{(k)} = P_+(A^{(k-1)} - \alpha_k \nabla f(A^{(k-1)}))$.
7: end for

FIG. 15

|  | $C_{S1}$ | $C_{S2}$ | $C_{S3}$ | ... | $C_{Sn}$ |
|---|---|---|---|---|---|
| $C_{D1}$ | 0.3 | 0.2 | 0.5 | ... | 0.1 |
| $C_{D2}$ | 0.2 | 0.1 | 0.1 | ... | 0.1 |
| $C_{D3}$ | 0.2 | 0.2 | 0.3 | ... | 0.5 |
| ... | ... | ... | ... | ... | ... |
| $C_{Dn}$ | 0.4 | 0.3 | 0.3 | ... | 0.1 |

FIG. 16

| TOP 10 DRUGS PREDICTED FOR AD | | |
|---|---|---|
| DRUG | PREDICTION SCORE | CLINICAL EVIDENCE? |
| SELEGILINE* | 0.7091 | - |
| CARBIDOPA | 0.6924 | NO |
| AMANTADINE | 0.6897 | NO |
| PROCYCLIDINE | 0.6826 | NO |
| VALPROIC ACID* | 0.6745 | - |
| METFORMIN | 0.6543 | YES |
| BEXAROTENE | 0.6426 | YES |
| NEOSTIGMINE | 0.6385 | NO |
| GALANTAMINE* | 0.6348 | - |
| NILVADIPINE | 0.6159 | YES |

FIG. 22

GENERATING DRUG REPOSITIONING HYPOTHESES BASED ON INTEGRATING MULTIPLE ASPECTS OF DRUG SIMILARITY AND DISEASE SIMILARITY

CROSS-REFERENCE TO RELATED APPLICATION

This application is based upon and claims priority from U.S. patent application Ser. No. 14/541,285 filed on Nov. 14, 2014, the entire contents of which is hereby incorporated by reference herein.

BACKGROUND

The present disclosure generally relates to drug repositioning, and more particularly relates to generating drug repositioning hypotheses based on integrating multiple aspects of drug similarities and disease similarities.

In response to the high and high risk associated with traditional de novo drug discovery, investigation of potential additional uses for existing drugs, also known as drug repositioning, has attracted increasing attention from both the pharmaceutical industry and the research community. Drug repositioning presents a promising avenue for identifying better and safer treatments without the full cost or time required for de novo drug development. Candidates for repositioning are usually either market drugs or drugs that have been discontinued in clinical trials for reasons other than safety concerns. Because the safety profiles of these drugs are known, clinical trials for alternative indications are cheaper, potentially faster, and carry less risk than de novo drug development. Any newly identified indications can be quickly evaluated from phase II clinical trials. Drug repositioning can also greatly reduce drug discovery and development time.

BRIEF SUMMARY

In one embodiment, a method for predicting drug-disease associations is disclosed. The method comprises accessing a plurality of disease similarity matrices and a plurality of disease similarity matrices. Each of the plurality of drug similarity matrices is associated with a different drug information source. Each of the plurality of disease similarity matrices is associated with a different disease information source. A known drug-disease association matrix is also accessed. The known drug-disease association matrix indicates if a given drug identified is known to treat a given disease. At least one drug-disease association prediction is generated based on the plurality of drug similarity matrices, the plurality of disease similarity matrices, and the known drug-disease association matrix. The at least one drug-disease association prediction identifies a previously unknown association between a given drug and a given disease, and a probability that the given disease is treatable by the given drug.

In another embodiment, an information processing system for predicting drug-disease associations is disclosed. The information processing comprises memory and at least one processor that is communicatively coupled to the memory. A drug repositioning manager is communicatively coupled to the memory and the at least one processor. The drug reposition manager configured to perform a method. The method comprises accessing a plurality of disease similarity matrices and a plurality of disease similarity matrices. Each of the plurality of drug similarity matrices is associated with a different drug information source. Each of the plurality of disease similarity matrices is associated with a different disease information source. A known drug-disease association matrix is also accessed. The known drug-disease association matrix indicates if a given drug identified is known to treat a given disease. At least one drug-disease association prediction is generated based on the plurality of drug similarity matrices, the plurality of disease similarity matrices, and the known drug-disease association matrix. The at least one drug-disease association prediction identifies a previously unknown association between a given drug and a given disease, and a probability that the given disease is treatable by the given drug.

In yet another embodiment, a computer program product for predicting drug-disease associations is disclosed is disclosed. The computer program product comprises a storage medium readable by a processing circuit and storing instructions for execution by the processing circuit for performing a method. The method comprises accessing a plurality of disease similarity matrices and a plurality of disease similarity matrices. Each of the plurality of drug similarity matrices is associated with a different drug information source. Each of the plurality of disease similarity matrices is associated with a different disease information source. A known drug-disease association matrix is also accessed. The known drug-disease association matrix indicates if a given drug identified is known to treat a given disease. At least one drug-disease association prediction is generated based on the plurality of drug similarity matrices, the plurality of disease similarity matrices, and the known drug-disease association matrix. The at least one drug-disease association prediction identifies a previously unknown association between a given drug and a given disease, and a probability that the given disease is treatable by the given drug.

BRIEF DESCRIPTION OF THE SEVERAL VIEWS OF THE DRAWINGS

The accompanying figures where like reference numerals refer to identical or functionally similar elements throughout the separate views, and which together with the detailed description below are incorporated in and form part of the specification, serve to further illustrate various embodiments and to explain various principles and advantages all in accordance with the present disclosure, in which:

FIGS. 2-4 provide various examples of drug similarity matrices according to one embodiment of the present disclosure;

FIGS. 5-7 provide various examples of disease similarity matrices according to one embodiment of the present disclosure;

FIG. 9 shows one example of a known drug-disease association matrix according to one embodiment of the present disclosure;

FIG. 10 shows one example of an algorithm for generating drug repositioning predictions/estimations according to one embodiment of the present disclosure;

FIG. 11 shows one example of a drug cluster assignment matrix according to one embodiment of the present disclosure;

FIG. 14 shows one example of an algorithm for performing a Projected Gradient calculation according to one embodiment of the present disclosure;

FIG. 15 shows one example of an algorithm for performing an Improved Projected Gradient calculation according to one embodiment of the present disclosure;

FIG. 16 shows one example of a disease-drug cluster relationship matrix according to one embodiment of the present disclosure;

FIG. 22 is a table showing the top 10 drugs identified by one or more embodiments for Alzheimer's Disease;

DETAILED DESCRIPTION

Figure 1:
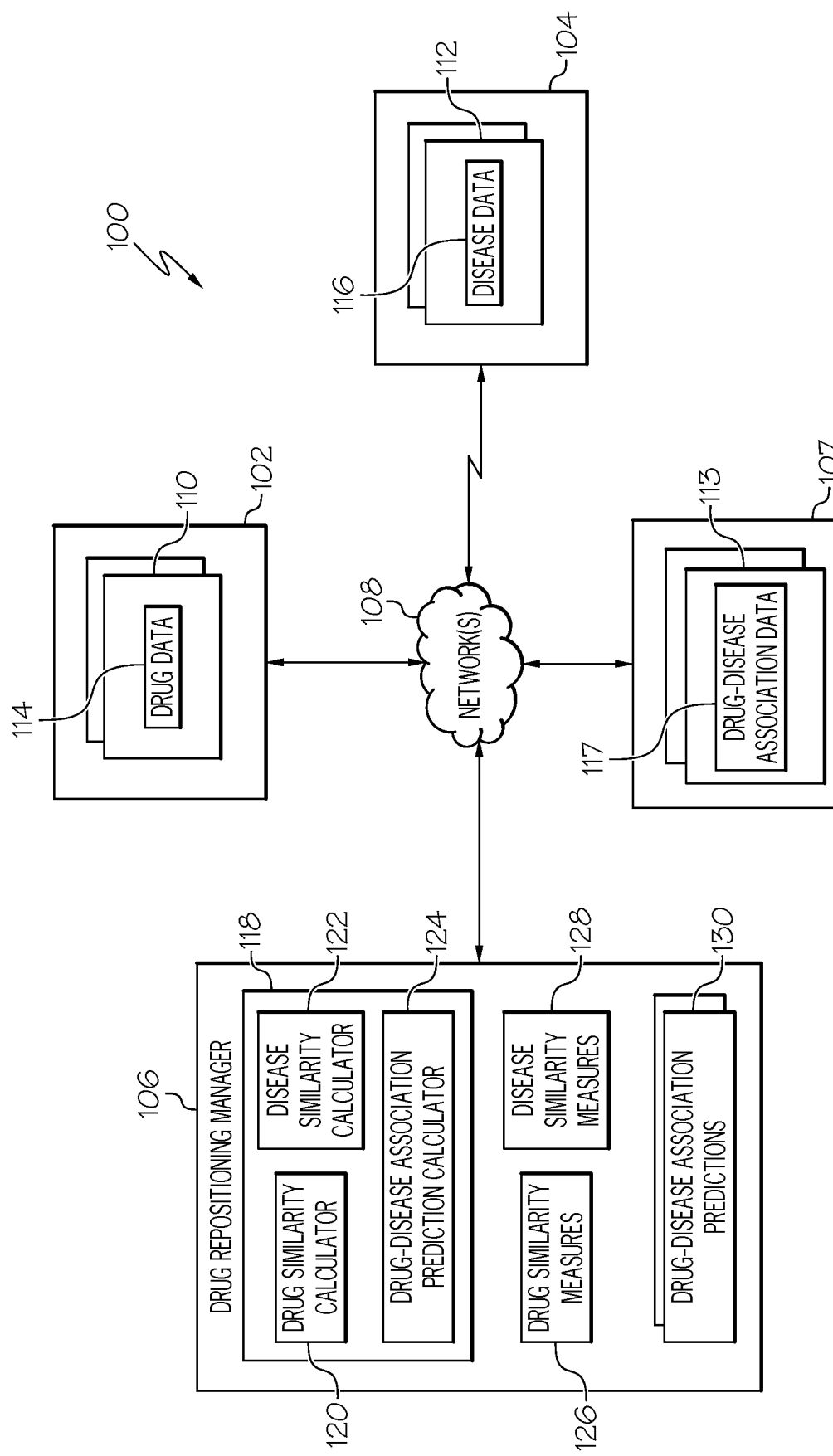
FIG. 1 is a block diagram illustrating one example of an operating environment according to one embodiment of the present disclosure.

The inefficiency of pharmaceutical drug development with high expenditure but low productivity has been widely discussed. Drug repositioning, which is the process of finding additional indications (i.e., diseases) for existing drugs, presents a promising avenue for identifying better and safer treatments without the full cost or time required for de novo drug development. Candidates for repositioning are usually either market drugs or drugs that have been discontinued in clinical trials for reasons other than safety concerns. Because the safety profiles of these drugs are known, clinical trials for alternative indications are cheaper, potentially faster, and carry less risk than de novo drug development. Any newly identified indications can be quickly evaluated from phase II clinical trials. Drug repositioning can reduce drug discovery and development time from an average of 10-17 years to potentially 3-12 years. Therefore, it is not surprising that in recent years, new indications, new formulations, and new combinations of previously marketed products accounted for more than 30% of the new medicines that reach their first markets. Drug repositioning has drawn widespread attention from the pharmaceutical industry, government agencies, and academic institutes. However, current successes in drug repositioning have primarily been the result of serendipitous events based on ad hoc clinical observation, unfocused screening, and "happy accidents". Comprehensive and rational approaches are urgently needed to explore repositioning opportunities.

Accordingly, one or more embodiments provide a unified computational framework for drug repositioning hypothesis generation by integrating multiple Drug information sources and multiple Disease information sources to facilitate drug Repositioning tasks (DDR). At least one embodiment utilizes drug similarity network, disease similarity network, and known drug-disease associations to analyze potential associations among other unlinked drugs and diseases. Various types of drug information (e.g., chemical structure, target protein, and side effects) and various types of disease information (e.g., phenotype, ontology, and disease gene) are utilized by various embodiments for drug repositioning hypothesis generation. These embodiments are extensible and can incorporate additional types of drug/disease information sources.

Embodiments of the present disclosure are advantageous over conventional drug repositioning methods because they are able to predict additional drug-disease associations by considering both drug information and disease information. In addition, various embodiments determine then interpretable importance of different information sources during the prediction. Also, various embodiments discover the drug and disease groups as by-products such that the drugs or diseases within the same group are highly correlated with each other. This provides additional insights for targeted downstream investigations including clinical trials.

FIG. 1 shows one example of an operating environment 100 for generating drug repositioning hypotheses. In the example shown in FIG. 1, the operating environment 100 comprises a plurality of information processing systems 102, 104, 106, 107. Each of the information processing systems 102, 104, 106, 107 is communicatively coupled to one or more networks 108 comprising connections such as wire, wireless communication links, and/or fiber optic cables. One or more of the information processing systems 102, 104, 107 provide information sources 110, 112, 113 comprising drug data 114, disease data 116, and known drug-disease association data 117. Examples of drug data include (but are not limited to) drug name, drug manufacturer, drug chemical structure, drug target protein, drug side effects, and/or the like. Examples of disease data included (but are not limited to) disease name, disease phenotype, disease ontology, disease genes, and/or the like. Known drug-disease association data 117 comprises information such as disease names and the known drugs that have been used or that are currently being used to treat each disease.

At least one of the information processing systems 106 comprises a drug repositioning manager 118. The drug repositioning manager 118 comprises a drug similarity calculator 120, a disease similarity calculator 122, and a drug repositioning hypothesis/prediction generator 124. The drug similarity calculator 120 generates drug similarity measures 126 for various drugs based on drug data 114 obtained from the information sources 110. The disease similarity calculator 120 generates disease similarity measures 128 for various diseases based on disease data 116 obtained from the information sources 112. The drug repositioning hypothesis/prediction generator 124 predicts and generates drug-disease associations 130 by considering both the generated drug and disease similarity measures 126, 128. The methods, operations, and processes performed by the prediction generator 124 are herein referred to as "DDR". The drug repositioning manager 118 and its components are discussed in greater detail below.

In one embodiment, the drug repositioning manager 118 automatically obtains the drug and disease data 114, 116 from the information sources 110, 112. For example, the drug repositioning manager 118 can automatically query (or perform a data pull operation) the information sources 110, 112 for drug and disease data 114, 116 at predefined intervals or based upon receiving a command from a user interacting with the information processing system 106. In another example, the drug the information sources 110, 112 automatically push the drug and disease data 114, 116 to the repositioning manager 118 at predefined intervals, based upon the data 114, 116 being updated, and/or the like. Once drug and disease data 114, 116 is obtained, the drug and disease similarity calculators 120, 122 calculate drug and similarity measures 124, 126, respectively.

In one embodiment, drug/disease similarities 124, 126 are utilized by the drug repositioning manager 118 to quantify the degree of common characteristics shared between pairs of drugs/diseases. For example, a drug or disease similarity calculated for a pair of drugs or diseases is a score that ranges from 0 to 1, with 0 representing the lowest similarity and 1 representing the highest similarity. It should be noted that embodiments are not limited to these scores and other representations are applicable as well. The drug similarity calculator 124 calculates various types of drug similarity measures including (but not limited to) similarity measures based on chemical structures, target proteins, and side effects. The disease similarity calculator 122 calculates various types of disease similarity measures including (but not limited to) similarities based on disease phenotypes, disease ontology, and disease genes.

Drugs with similar chemical structures will likely carry out common therapeutic functions and treat common diseases. Therefore, the drug similarity calculator 124 calculates a first drug pairwise similarity measure, $D^{chem}$, based on a chemical structure fingerprint corresponding to the substructures of the drugs. In one embodiment, the 881 chemical substructures defined in the PubChem database are utilized to calculate the $D^{chem}$ similarity. In this embodiment, each drug d is represented by an n-dimensional binary profile h(d) (e.g., an 881-dimensional binary profile) whose elements encode for the presence or absence of each chemical substructure by 1 or 0, respectively. Then the pairwise chemical similarity between two drugs d and d' is computed by the drug similarity calculator 120 as the Tanimoto efficient of their chemical fingerprints:

$$D_{d,d'}^{chem} = \frac{h(d) \Box h(d')}{|h(d)| + |h(d')| - h(d) \Box h(d')}, \quad (EQ\ 1)$$

where |h(d)| and |h(d')| are the counts of substructure fragments in drugs d and d' respectively. The dot product h(d)□h(d') represents the number of substructure fragments shared by two drugs. The drug similarity calculator 120 then generates an n×n drug similarity matrix $D_{chem}$. FIG. 2 shows one example of this similarity matrix 200 where each element of the matrix 200 comprises the similarity measure/score between two drugs based on their chemical structures. For example, FIG. 2 shows that the matrix 200 includes an element 202 comprising the similarity measure of $D_{12}^{chem}$ for drugs $d_1$ and $d_2$.

Figure 3:
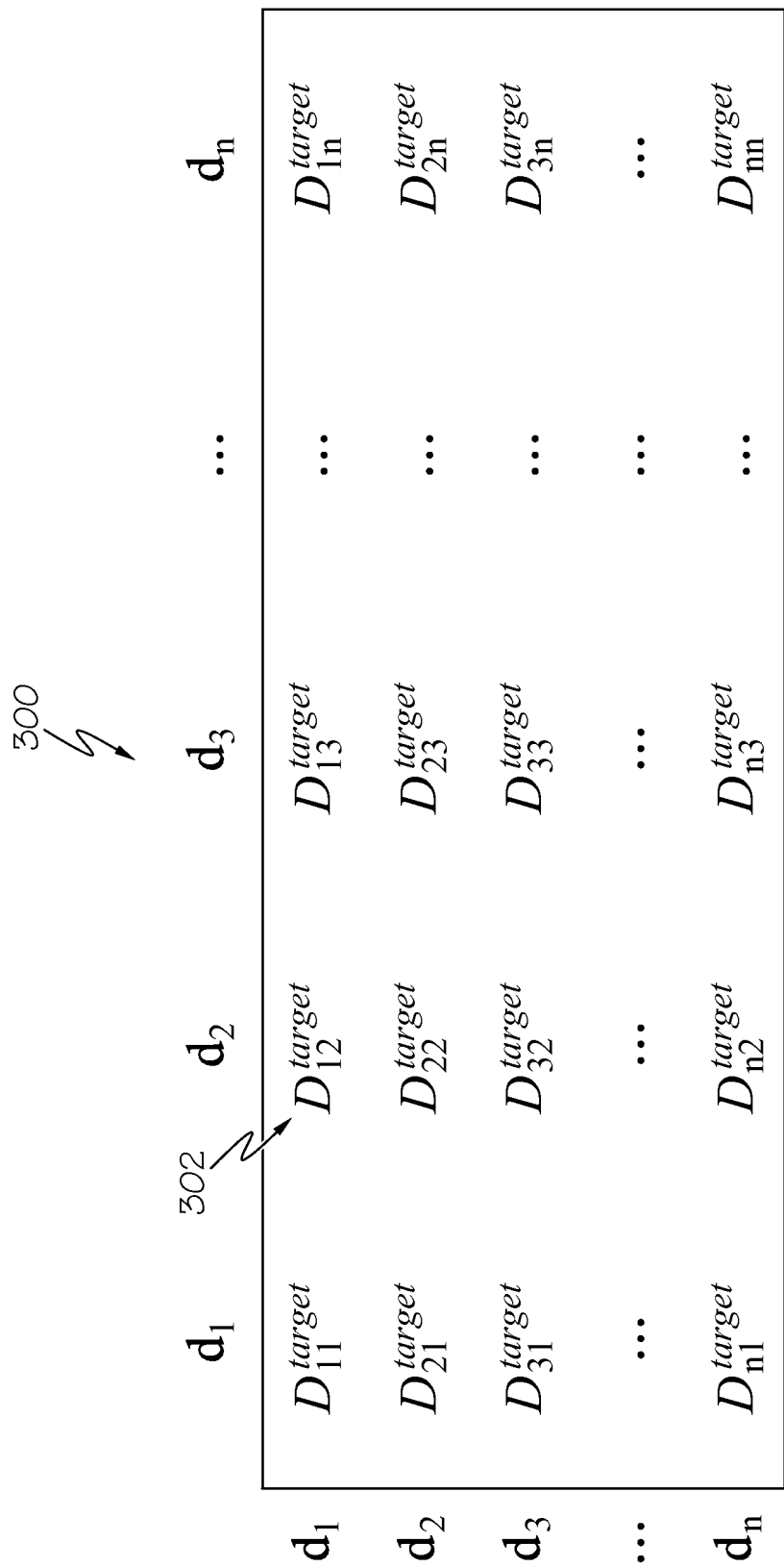

A send drug pairwise similarity measure calculated by the drug similarity calculator 124 is a target protein similarity measure, $D^{target}$. A drug target is the protein in the human body whose activity is modified by a drug resulting in a desirable therapeutic effect. Drugs sharing common targets often possess similar therapeutic function. After the drug repositioning manager 118 obtains drug data 114 comprising target protein information the drug similarity calculator 124 calculates the pairwise drug target similarity between drugs d and d' based on the average of sequence similarities of their target protein sets according to:

$$D_{d,d'}^{target} = \frac{1}{|P(d)||P(d')|} \sum_{i=1}^{|P(d)|} \sum_{j=1}^{|P(d')|} SW(P_i(d), P_j(d')), \quad (EQ\ 2)$$

where given a drug d, the drug similarity calculator 124 presents its target protein set as P(d); then |P(d)| is the size of the target protein set of drug d. The sequence similarity function of two proteins SW is calculated by the drug similarity calculator 120 as a Smith-Waterman sequence alignment score. The drug similarity calculator 120 then generates an n×n drug similarity matrix $D_{target}$ FIG. 3 shows one example of this similarity matrix 300 where each element of the matrix 300 comprises the similarity measure/score between two drugs based on their target proteins. For example, FIG. 3 shows that the matrix 300 includes an element 302 comprising the similarity measure of $D_{12}^{target}$ for drugs $d_1$ and $d_2$.

A third drug pairwise similarity measure calculated by the drug similarity calculator 124 is a drug side effect similarity measure, $D^{se}$. Drug side effects, or adverse drug reactions, indicate the malfunction by off-targets. Thus, side effects are useful to infer whether two drugs share similar target proteins and treat similar diseases. Once the drug repositioning manager 118 obtains drug data 114 comprising side effect information the drug similarity calculator 124 represents each drug d by an y-dimensional binary side effect profile e(d) (e.g., a 4192-dimensional binary side effect profile e(d)) whose elements encode for the presence or absence of each of the side effect key words by 1 or 0 respectively. Then, the pairwise side effect similarity between two drugs d and d' is computed by the drug similarity calculator 120 as the Tanimoto efficient of their side effect profiles:

$$D_{d,d'}^{se} = \frac{e(d) \Box e(d')}{|e(d)| + |e(d')| - e(d) \Box e(d')}, \quad (EQ\ 3)$$

where |e(d)| and |e(d')| are the counts of side effect keywords for drugs d and d' respectively. The dot product e(d)□e(d') represents the number of side effects shared by two drugs. The drug similarity calculator 120 then generates an n×n drug similarity matrix $D_{se}$. FIG. 4 shows one example of this similarity matrix 400 where each element of the matrix 400 comprises the similarity measure/score between two drugs based on their side effects. For example, FIG. 4 shows that the matrix 400 includes an element 402 comprising the similarity measure of $D_{12}^{se}$ for drugs $d_1$ and $d_2$.

In one embodiment, the disease similarity calculator 126 calculates a first pairwise disease similarity measure, $S^{pheno}$, based on disease phenotypes. Disease phenotypes indicate phenotypic abnormalities encountered in human diseases. After the drug repositioning manager 118 obtains disease data 116 comprising drug phenotype information, the disease similarity calculator 122 constructs a disease phenotypic similarity measure for two or more diseases by identifying the similarity between various terms associated with the diseases. For example, if the information source 112 is a knowledge base of human genes and genetic disorders such as the Online Mendelian Inheritance in Man (OMIM), the disease similarity calculator 122 identifies the similarity between the Medical Subject Headings (MeSH) appearing in the medical description ("full text" and "clinical synopsis" fields) of diseases from the OMIM database. In this embodiment, each disease s obtained from the disease data 116 is represented by a K-dimensional (K is the number of the terms) term feature vector m(s). Each entry in the feature vector represents a term of interest (e.g., MeSH terms), and the counts of the term found for disease s are the corresponding feature value. Then the pairwise disease phenotype similarity between two diseases s and s' is computed by the disease similarity calculator 122 as the sine of the angle between their feature vectors:

$$S_{ss'}^{pheno} = \frac{\sum_{i=1}^{K} m(s)_i m(s')_i}{\sqrt{\sum_{i=1}^{K} m^2(s)_i} \sqrt{\sum_{i=1}^{K} m^2(s')_i}}, \quad (EQ\ 4)$$

where $m(s)_i$ denotes the i-th entry of the feature vector m(s). The disease similarity calculator 122 then generates an n×n disease similarity matrix $S_{pheno}$. FIG. 5 shows one example of this similarity matrix 500 where each element of the matrix 500 comprises the similarity measure/score between two diseases based on their phenotypes. For example, FIG. 5 shows that the matrix 500 includes an element 502 comprising the similarity measure of $S_{12}^{pheno}$ for diseases $s_1$ and $s_2$.

Figure 6:
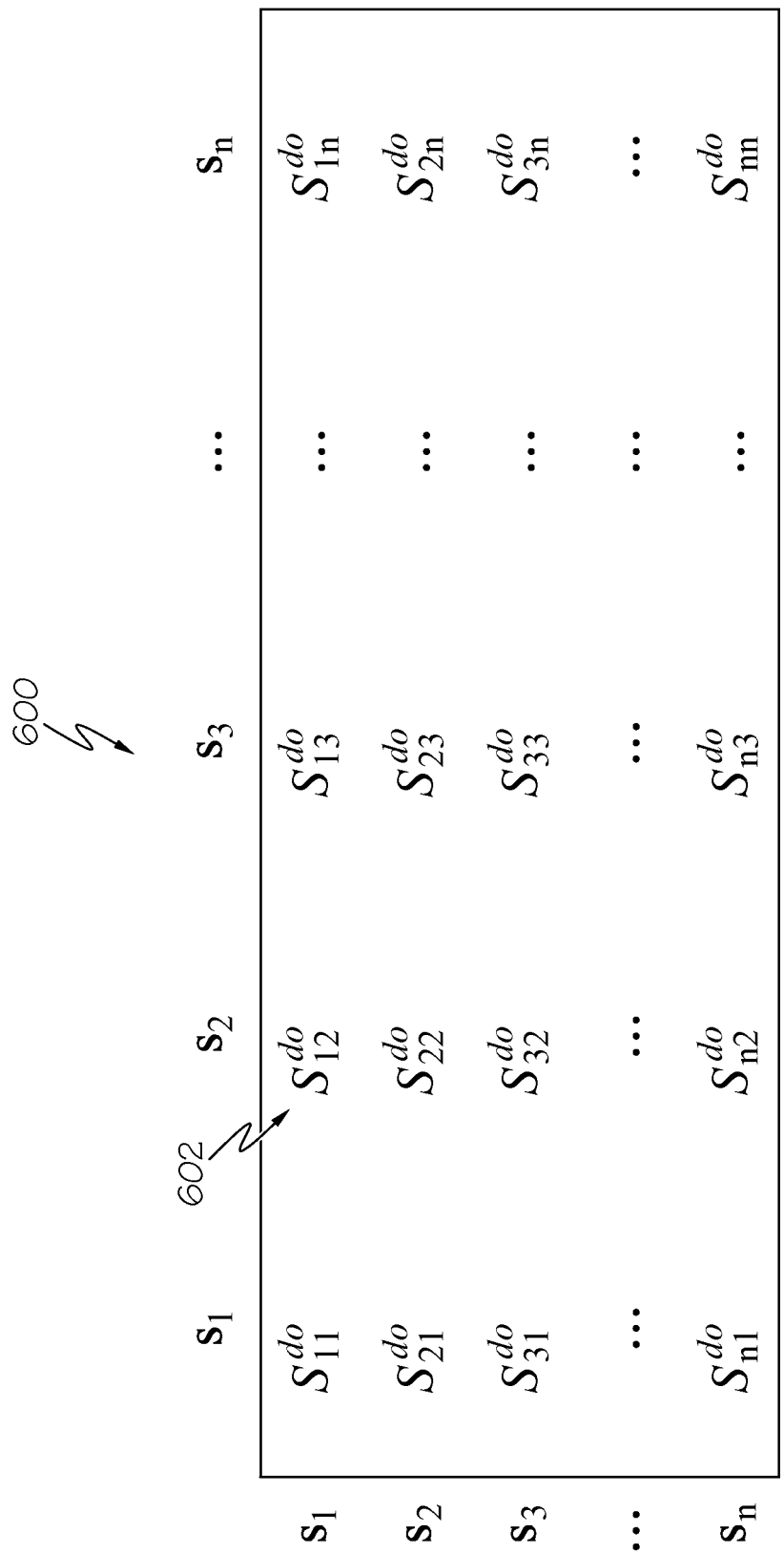

A send pairwise disease similarity measure calculated by the disease similarity calculator 122 is a disease ontology similarity measure, $S^{do}$. The drug repositioning manager 118 obtains disease data 116 comprising disease ontology information form an information source 112 such as (but not limited to) the Disease Ontology (DO). The Disease Ontology (DO) is an open source ontological description of human disease that is organized from a clinical perspective of disease etiology and location. The terms in DO are disease names or disease-related concepts and are organized in a directed acyclic graph (DAG). Two linked diseases in DO are in an "is-a" relationship, which means one disease is a subtype of the other linked disease, and the lower a disease is in the DO hierarchy, the more specific the disease term is. The disease similarity calculator 122 utilizes the obtained disease data 116 to calculate the semantic similarity between any pair of the diseases. In one embodiment, for a disease term s in disease data 116, the probability that the term is used in disease annotations is estimated as $p_s$, which is the number of disease term s or its descendants in the disease data 116 divided by the total number of disease terms in the disease data 116. Then the semantic similarity of two diseases s and s' is defined as the information content of their lowest common ancestor by:

$$S_{ss'}^{do} = -\log \min_{x \in C(s,s')} p_x, \quad (EQ\ 5)$$

where C(s,s') is the set of all common ancestors of diseases s and s'. The disease similarity calculator 122 then generates an n×n disease similarity matrix $S_{do}$. FIG. 6 shows one example of this similarity matrix 600 where each element of the matrix 600 comprises the similarity measure/score between two diseases based on their ontology information. For example, FIG. 6 shows that the matrix 600 includes an element 602 comprising the similarity measure of $S_{12}^{do}$ for diseases $S_1$ and $s_2$.

Figure 7:
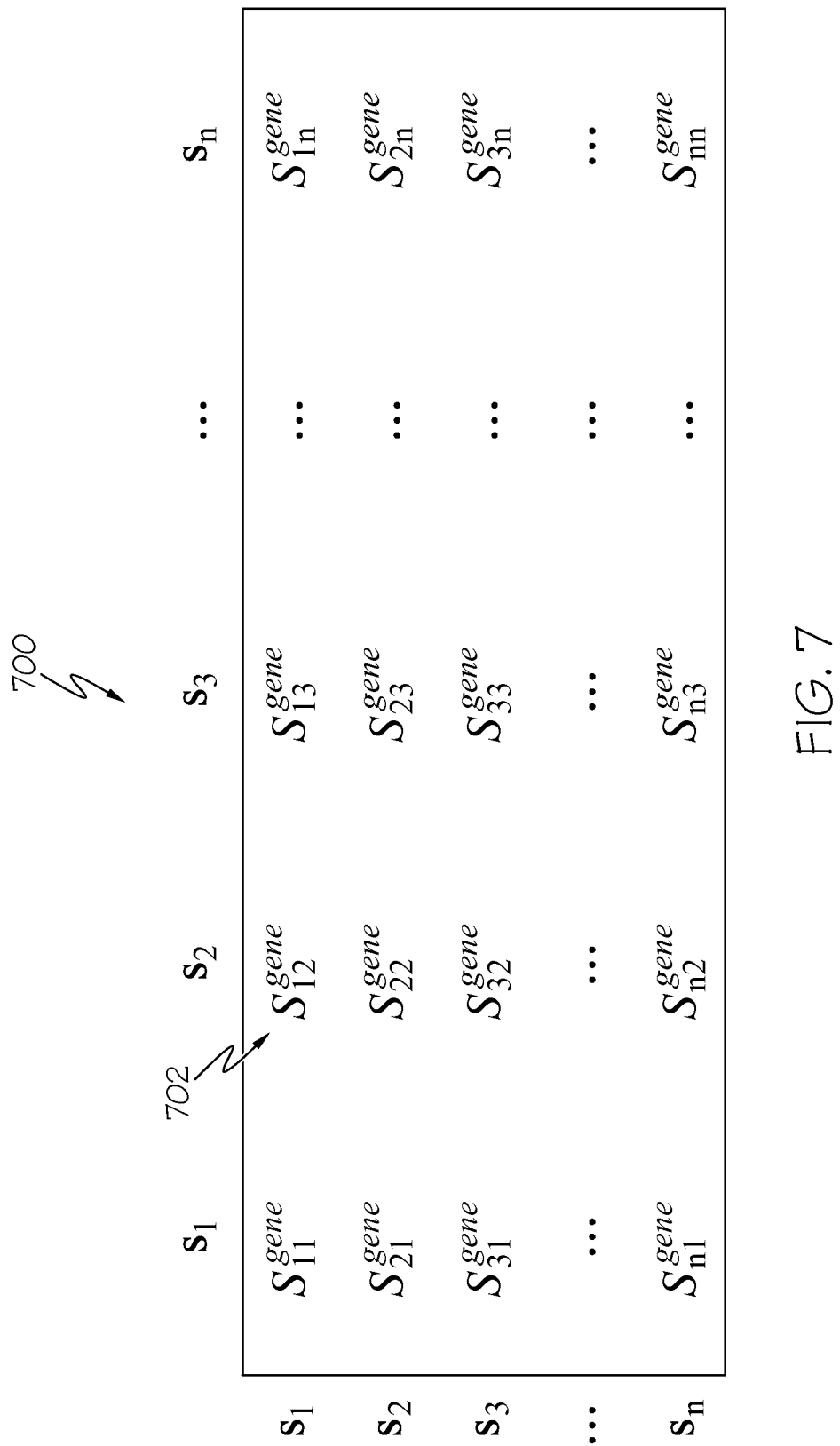

A third disease similarity measure, $S^{gene}$, calculated by the disease similarity calculator 122 is based on disease genes. Disease-causing aberrations in the normal function of a gene define that gene as a disease gene. In this embodiment, the drug repositioning manager 118 obtains disease data 116 comprising disease gene information. For example, the drug repositioning manager 118 collects all disease genes for each disease from "phenotype-gene relationships" field from the OMIM database. The disease similarity calculator 122 calculates the pairwise disease similarity between diseases s and s' based on the average of sequence similarities of their disease gene sets as defined by:

$$S_{ss'}^{gene} = \frac{1}{|G(s)||G(s')|} \sum_{i=1}^{|G(s)|} \sum_{j=1}^{|G(s')|} SW(G_i(s), G_j(s')), \quad (EQ\ 6)$$

where given a disease s, the disease similarity calculator 126 presents its disease gene set as G(s); then |G(s)| is the size of the disease gene set of disease s. The sequence similarity function of two disease genes SW, in one embodiment, is calculated by the disease similarity calculator 122 as a Smith-Waterman sequence alignment score. The disease similarity calculator 122 then generates an n×n disease similarity matrix $S_{gene}$. FIG. 7 shows one example of this similarity matrix 700 where each element of the matrix 700 comprises the similarity measure/score between two diseases based on their genes. For example, FIG. 7 shows that the matrix 700 includes an element 702 comprising the similarity measure of $S_{12}^{gene}$ for diseases $s_1$ and $s_2$.

Figure 8:
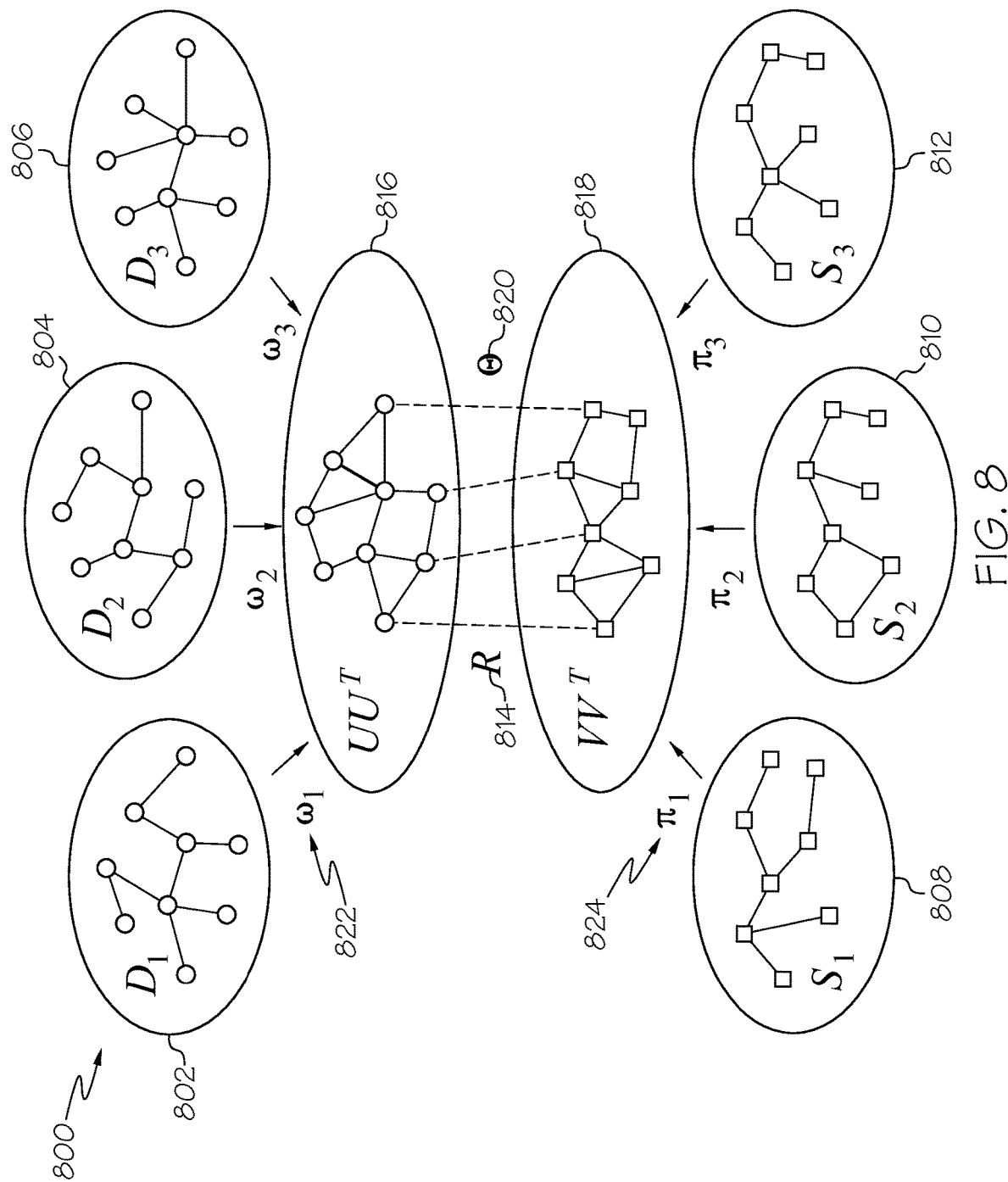
FIG. 8 is a graphical representation of generating drug repositioning predictions/estimations according to one embodiment of the present disclosure.

The drug and disease similarity matrices discussed above and known drug-disease associations 117 are inputted into the drug repositioning prediction generator 124. The drug repositioning prediction generator 124 utilizes these inputs to generate one or more drug repositioning predictions 130, latent drug groupings, latent disease groupings, and an importance weighting for information sources. For example, FIG. 8 shows a graphical representation 800 of an overall process for generating one or more drug repositioning predictions 130 according to at least one embodiment of the present disclosure. In the example shown in FIG. 8, the drug repositioning prediction generator 124 takes as input a plurality of drug similarity matrices (networks) $D_1$ 802, $D_2$ 804, and $D_n$, 806; a plurality of disease similarity matrices (networks) $S_1$ 808, $S_2$ 810, and $S_n$, 812; and a known/observed drug-disease association matrix R 814. The known/observed drug-disease association matrix R 814 is generated by the drug repositioning prediction generator 124 based on obtained drug-disease association data 113. For example, the prediction generator 124 analyze and parses the drug-disease association data 113 and identifies which drugs are being used (or have been previously used) to treat a given disease. The prediction generator 124 then generates a matrix 814 comprising these associations.

Figure 9:
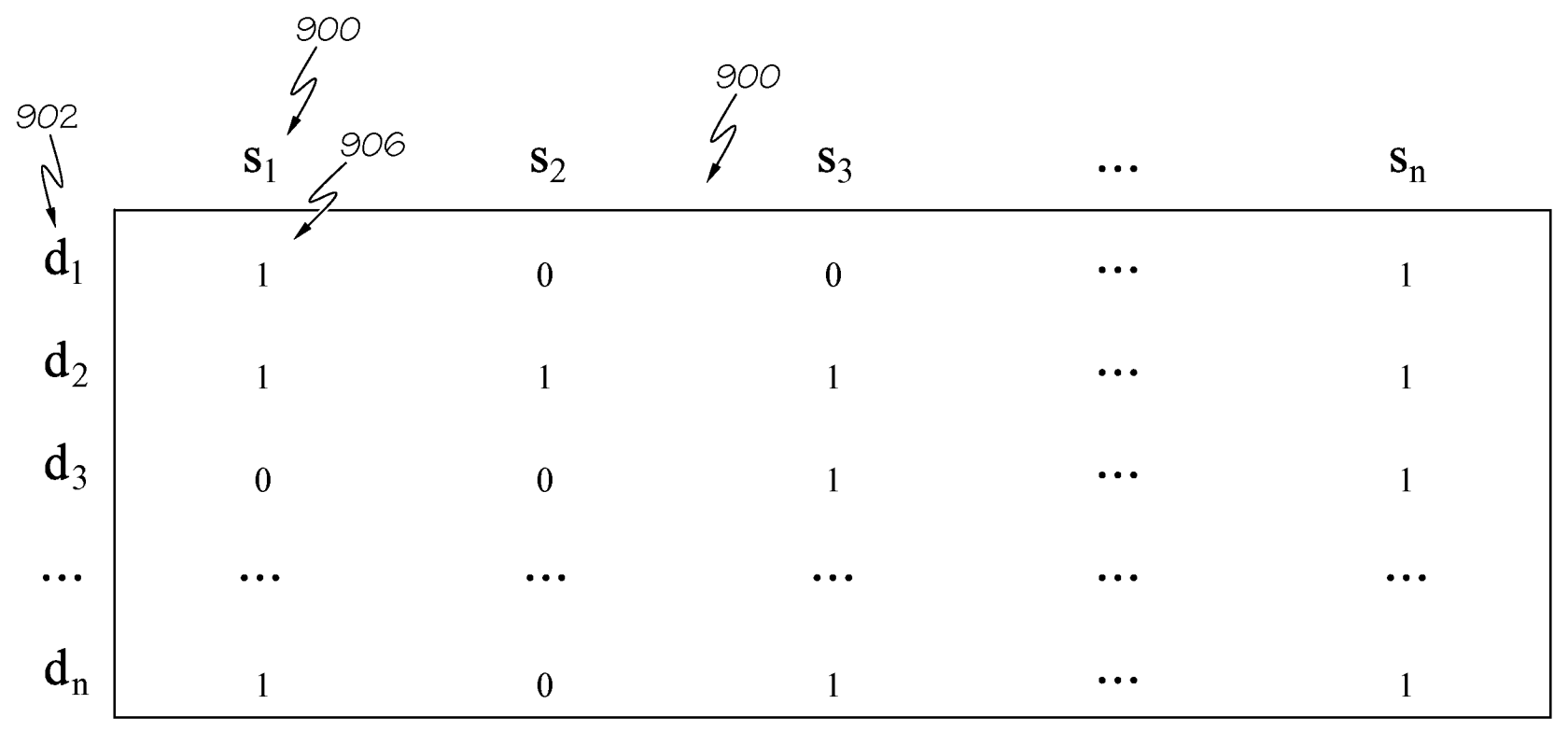

The known/observed drug-disease association matrix R 814 is a matrix with each row representing a given drug and each column representing a given disease (or vice versa). Each element in the matrix indicates whether the drug-disease combination has a known association. For example, FIG. 9 shows one example of a known/observed drug-disease association matrix R 900 generated by the prediction generator 124. In this example, each row 902 corresponds to a drug d and each column 904 corresponds to a disease s. If an element 906 of a given row/column comprise a value of "1", this indicates that the associated drug and disease have a known association (i.e., the drug is used or has been used to treat the disease). If an element 906 of a given row/column comprise a value of "0", this indicates that the associated drug and disease do not have a known association (i.e., the drug is not currently being used or has not been previously used to treat the disease). It should be noted that other values/characters besides "1" and "0" can be utilized to indicate a known drug-disease association or the absence thereof.

Returning now to FIG. 8, the prediction generator 124 utilizes the drug similarity matrices $D_1$ 802, $D_2$ 804, and $D_n$ 806; plurality of disease similarity matrices $S_1$ 808, $S_2$ 810, and $S_n$, 812; and the known/observed drug-disease association matrix R 814 to learn a drug/disease grouping matrix U or V, an estimated drug similarity matrix $UU^T$ 816, an estimated disease similarity matrix $VV^T$ 818, an estimated drug-disease association matrix $\Theta$ 820, and an importance factor $\omega$ 822 or $\pi$ 824 of different drug/disease information sources. The estimated drug-disease association matrix $\Theta$ comprises new drug-disease associations identified by the prediction generator 124. Stated differently, the prediction generator 124 identifies one or more drugs that can be utilized to treat a given disease(es) where the identified drug(s) is not currently being used or has not been previously used to treat the given disease(s).

In particular, assume there are n information sources to measure drug similarity, m information sources to measure disease similarity, and a total of $K_d$ information sources to measure the drug similarities, and a total of $K_s$ sources to measure the disease similarities. Let $D_k \in \mathbb{R}^{n \times n}$ be a drug similarity matrix measured on the k-th information source. Similarly, let $S_l \in \mathbb{R}^{m \times m}$ be a disease similarity matrix measured on the l-th information source. Let $U \in \mathbb{R}^{n \times C_D}$ a latent drug grouping matrix with $C_D$ being the number of drug groups, and $U_{ij}$ indicating the possibility that the i-th drug belongs to the j-th drug cluster. Let $V \in \mathbb{R}^{m \times C_s}$ be a latent disease grouping matrix with $C_s$ the number of disease groups, and $V_{ij}$ indicating the possibility that the i-th disease belongs to the j-th disease cluster. Let $R \in \mathbb{R}^{n \times m}$ be an observed (i.e., known) drug-disease association matrix with $R_{ij}=1$ if the association between the i-th drug and j-th disease is observed, and $R_{ij}=0$ otherwise.

Based on the above, the prediction generator 124 integrates multiple drug similarities, multiple disease similarities, and known drug-disease associations to calculate a global estimation on the entire drug-disease network including the intrinsic drug similarity, intrinsic disease similarity, as well as drug-disease associations. The prediction generator 124 formulates such a network estimation problem as a constrained nonlinear optimization problem. For example, the prediction generator 124 analyzes the drug-disease network comprising the drug and disease matrices generated by the prediction generator 124 by minimizing the following objective:

$$J = J_0 + \lambda_1 J_1 + \lambda_2 J_2 \quad \text{(EQ 7)},$$

where $\lambda_1$ and $\lambda_2$ are user-defined weighting factors for $J_1$ and $J_2$, respectively, and indicate how much weight is to be given to their respective part of the objective.

The objective in EQ 7 has three parts: $J_0$, $J_1$ and $J_2$. $J_0$ is the reconstruction loss of observed drug-disease associations and is defined as follows:

$$J_0 = \|\Theta - U\Lambda V^T\|_F^2 \quad \text{(EQ 8)}.$$

Here, $\Theta \in \mathbb{R}^{n \times m}$ is the estimated dense version of R, $\Lambda \in \mathbb{R}^{C_D \times C_s}$ encodes the relationship between drug clusters and disease clusters, and $\|\cdot\|_F$ denotes Frobenius norm of a matrix.

$J_1$ is the reconstruction loss of drug similarities and is defined as follows:

$$J_1 = \Sigma_{k=1}^{K_d} \omega_k \|D_k - UU^T\|_F^2 + \delta_1 \|\omega\|_2^2 \quad \text{(EQ 9)}.$$

Here, the estimated drug similarity matrix is $UU^T$, and $\omega \in \mathbb{R}^{K_d \times 1}$ is the non-negative weight vector when aggregating the reconstruction loss on different drug information sources. $UU^T$ is matrix that integrates the drug similarity matrices 802, 804, 806 generated by the prediction manager 124 based on heterogeneous information sources. The $L_2$ norm regularization is added to avoid trivial solution and $\delta_1 \geq 0$ is the tradeoff parameter.

$J_2$ is the reconstruction loss of disease similarities and is defined as follows:

$$J_2 = \Sigma_{l=1}^{K_s} \pi_l \|S_l - VV^T\|_F^2 + \delta_2 \|\omega\|_2^2 \quad \text{(EQ 10)}.$$

Here, the estimated disease similarity matrix is $VV^T$, and $\pi \in \mathbb{R}^{K_s \times 1}$ is the non-negative weight vector when aggregating the reconstruction loss on different disease information sources. $VV^T$ is matrix that integrates the disease similarity matrices 808, 810, 812 generated by the prediction manager 124 based on heterogeneous information sources. The $L_2$ norm regularization is added for the same reasons as in equation (EQ 9).

Combining the above, the prediction generator 124 resolves the following optimization problem:

$$\min_{U,V,\Lambda,\Theta,\omega,\pi} J \quad \text{(EQ 11)},$$

subject to $U \geq 0$, $V \geq 0$, $\Lambda \geq 0$, $\omega \geq 0$, $\omega^T 1 = 1$, $\pi^T 1 = 1$, $P_\Omega(\Theta) = P_\Omega(R)$, where $\Omega$ is the set of indices of the observed associations, and $P_\Omega$ is the projection operator on obtaining the entries of a matrix indexed by the indices in $\Omega$. Thus, the constraint $P_\Omega(\Theta) = P_\Omega(R)$ restricts the estimated drug-disease associations should include the ones that are already observed. Note that to enhance the interpretability of the learned model, U, V, and $\Lambda$, in one embodiment, are non-negative and w and it are in simplexes. Table 1 below lists the various notations and symbols discussed above.

TABLE 1

| Notation | Size | Meaning |
| --- | --- | --- |
| $D_k$ | n × n | The k-th drug similarity matrix |
| $S_l$ | m × m | The l-th disease similarity matrix |
| U | n × $C_D$ | Drug cluster assignment matrix |
| V | m × $C_S$ | Disease cluster assignment matrix |
| $\Lambda$ | $C_D$ × $C_S$ | Drug-disease cluster relationship matrix |
| R | n × m | Observed drug-disease association matrix |
| $\Theta$ | n × m | Densified estimation of R |
| $\omega$ | $K_d$ × 1 | Drug similarity weight vector |
| $\pi$ | $K_s$ × 1 | Disease similarity weight vector |

Since there are multiple groups of variables involved in the optimization problem (EQ 11), the prediction generator 124 utilizes an efficient solution based on the Block Coordinate Descent (BCD) strategy. Therefore, in one embodiment, the prediction generator 124 solves the different groups of variables alternatively until convergence. In one embodiment, convergence occurs when the reconstruction losses $J_0$, $J_1$, and $J_2$ no longer decrease. At each iteration, the prediction generator 124 solves the optimization problem with respect to one group of variables with all other groups of variables fixed.

The following is a more detailed discussion on how the prediction generator 124 iteratively solves the optimization problem of EQ 11 by integrating multiple drug similarities, multiple disease similarities, and known drug-disease associations. As discussed above, this DDR process allows the prediction generator 124 to achieve a global estimation on the entire input drug-disease network including new drug-disease associations, intrinsic drug similarity, and intrinsic disease similarity. FIG. 10 shows one example of an algorithm 1000 illustrating an overall process performed by the prediction generator 124 to identify new drug-disease associations, the interpretable importance of different information sources, and drug and disease groups. In one embodiment, the prediction generator 124 is programmed to perform the operations shown in the algorithm 1000.

The prediction generator 124 utilizes the drug matrices $\{D_k\}_{k=1}^{K_d}$, the disease matrices $\{S_l\}_{l=1}^{K_t}$, and the known drug-disease association matrix R as inputs to perform the operations shown in FIG. 10. In addition, FIG. 10 shows that the user-defined weighting factors $\lambda_1$ and $\lambda_2$, the tradeoff parameters $\delta_1$ and $\delta_2$, the $K_d$ drug information sources, and the $K_s$ disease information sources are to be greater or equal to 0. Once the prediction generator 124 has received/generated its input it initializes various variables in the objective function EQ 10. For example, the prediction generator 124 initializes $\omega=(1/K_d)1\in\square^{K_d \times 1}$ and $\pi=(1/K_s)1\in\square^{K_s \times 1}$. In other words, the importance factors $\omega$ for each of the drug information sources (e.g., drug chemical structure, drug target protein, drug side effects) are initially set equal to each other, and the importance factors $\pi$ for each of the disease information sources (e.g., disease name, disease phenotype, disease ontology, disease genes) are initially set equal to each other.

Figure 11:
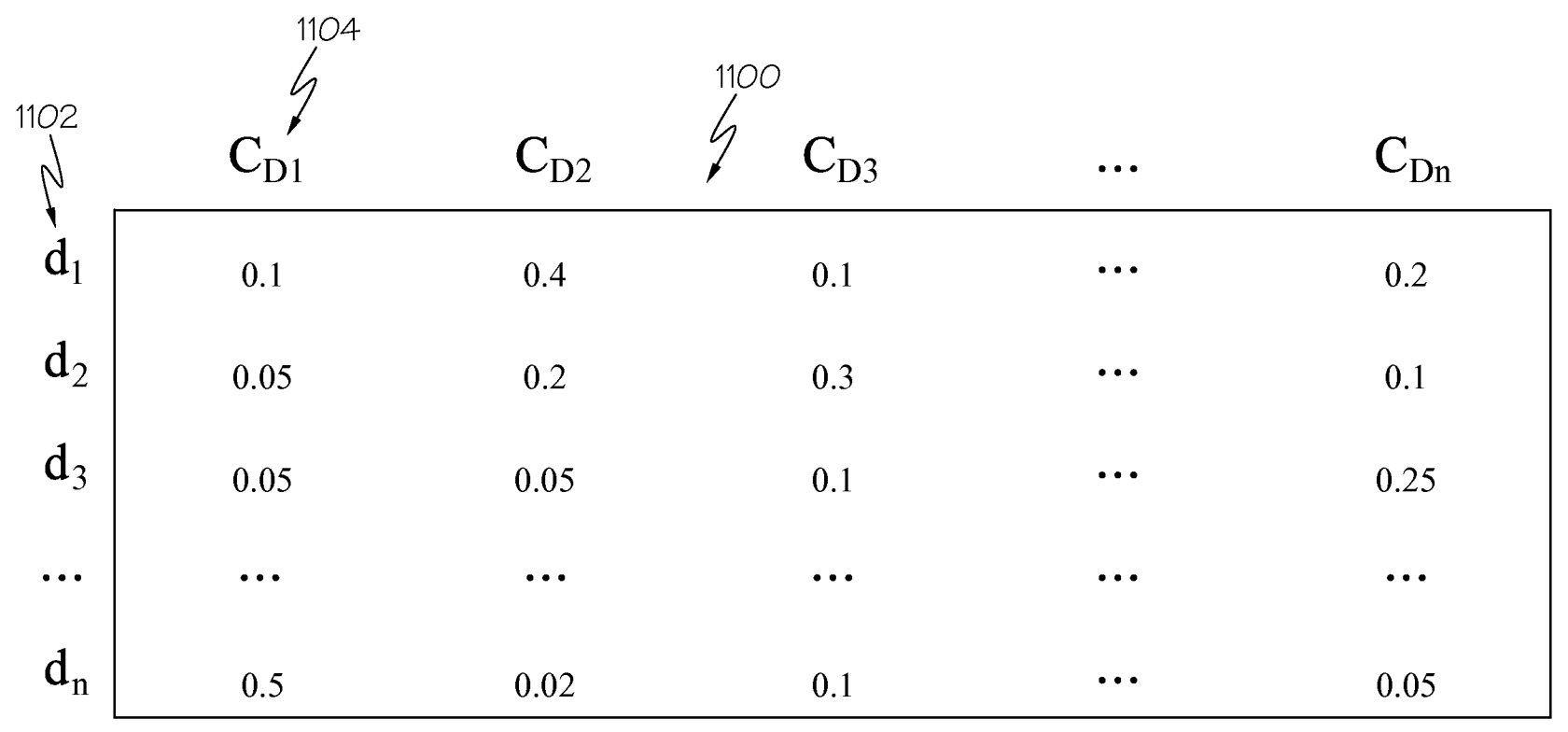
Figure 12:
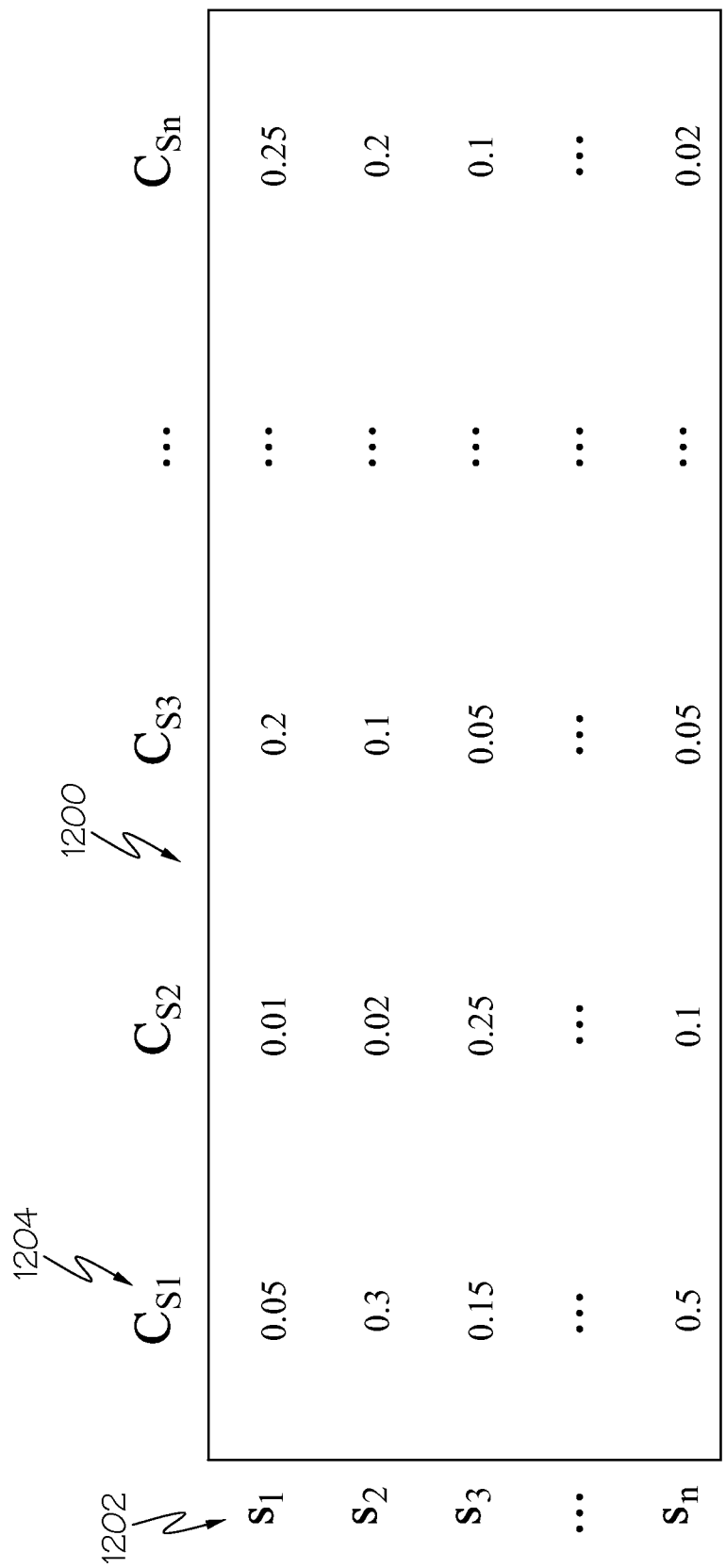
FIG. 12 shows one example of a disease cluster assignment matrix according to one embodiment of the present disclosure.

The prediction generator 124 initializes the disease cluster relationship matrix $\Lambda$ by populating the matrix with random values. The prediction generator 124 initializes the drug cluster assignment matrix U and the disease cluster assignment matrix V by performing Symmetric Non-negative Factorization on $\tilde{D}=\Sigma_{k=1}^{K_d}\omega_k D_k$ and $\tilde{S}=\Sigma_{l=1}^{K_s}\pi_l S_l$. One method of Symmetric Non-negative Factorization that is applicable for initializing U and V is given by Wang et al., "Community Discovery Using Nonnegative Matrix Factorization", Data Min Knowl Discov 22: 493-521 (2011), which is hereby incorporated by reference in its entirety. FIGS. 11 and 12 show examples of a drug cluster assignment matrix U 1100 and a disease cluster assignment matrix V 1200, respectively, after being initialized. In the example shown in FIG. 11, each row 1102 of the matrix 1100 corresponds to a given drug d and each column 1104 corresponds to a given drug group/class $C_D$. In one embodiment, the number of drug groups/classes is user defined. An element 1106 of a given row/column within the drug cluster assignment matrix U 1100 indicates the probability that the dug represented by the given row belongs to the drug group/class represented by the given column, with the sum of the probabilities in a given row being equal to 1. For example, FIG. 11 shows that there is a 10% probability that drug $d_1$ belongs to the drug class $C_{D1}$, a 40% probability that drug $d_1$ belongs to the drug class $C_{D2}$, a 10% probability that drug $d_1$ belongs to the drug class $C_{D3}$, and a 20% probability that drug $d_1$ belongs to the drug class $C_{Dn}$. Therefore, drug $d_1$ is assigned to drug class $C_{D2}$ since it has the highest probability associated therewith, e.g., 40%.

In the example shown in FIG. 12, each row 1202 of the matrix 1200 corresponds to a given disease s and each column 1204 corresponds to a given disease group/class $C_S$. In one embodiment, the number of disease groups/classes is user defined. An element 1206 of a given row/column within the disease cluster assignment matrix V 1200 indicates the probability that the disease represented by the given row belongs to the disease group/class represented by the given column, with the sum of the probabilities in a given row being equal to 1. For example, FIG. 12 shows that there is a 5% probability that disease $s_1$ belongs to the disease class $C_{S1}$, a 1% probability that disease $s_1$ belongs to the disease class $C_{s2}$, a 2% probability that disease $s_1$ belongs to the disease class $C_{S3}$, and a 25% probability that disease $s_1$ belongs to the disease class $C_{Sn}$. Therefore, disease $s_1$ is assigned to drug class $C_{sn}$ since it has the highest probability associated therewith, e.g., 25%.

After the initialization process discussed above, the prediction generator 124 iteratively calculates the estimated drug-disease association matrix $\Theta$ (the densified estimation of R); the drug similarity weight vector w; the disease similarity weight vector $\pi$; the drug-disease cluster relationship matrix $\Lambda$; the drug cluster assignment matrix U; and the disease cluster assignment matrix V.

The prediction generator 124 first calculates the estimated drug-disease association matrix $\Theta$, which is a densified estimation of R. In one embodiment, the prediction generator 124 calculates $\Theta$ according to:

$$\min_\Theta \|\Theta-W\|_F^2, \text{subject to } P_\Omega(\Theta)=P_\Omega(R) \quad (\text{EQ 12}),$$

where $W=U\Lambda V^T$. This is a constrained Euclidean projection, and can be decoupled for every element in $\Theta$. Each subproblem has a closed form solution. By aggregating all solutions together, the prediction generator 124 obtains the matrix form representation of the solution as:

$$\Theta^*=P_{\Omega^c}(W)+P_\Omega(R) \quad (\text{EQ 13}),$$

where $\Omega^c$ is the complementary index set for $\Omega$.

Figure 13:
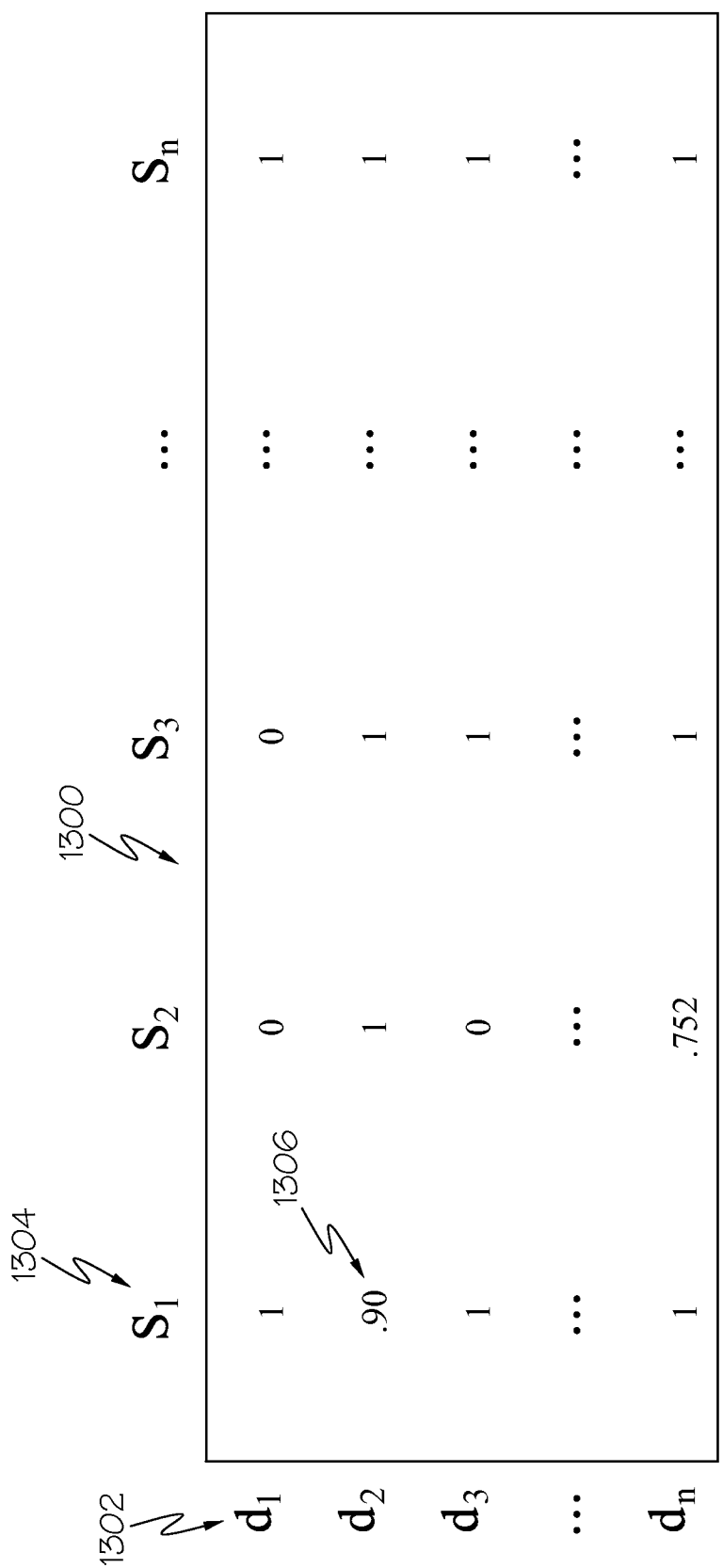
FIG. 13 shows one example of an estimated drug-disease association matrix according to one embodiment of the present disclosure.

FIG. 13 shows one example of an estimated drug-disease association matrix $\Theta$. The estimated drug-disease association matrix comprises new drug-disease associations calculated/identified by the prediction generator 124 based on the processes discussed above. In particular, $\Theta$ comprises new drug-disease associations that were not previously found in the known drug-disease association data or generated matrix. In this example, each row 1302 of the matrix 1300 corresponds to a drug d and each column 1304 corresponds to a disease s. If the value of each element 1306 in a given row/column indicates the probability that given drug can be used to treat the given disease. A value of 0 indicates that there is no likelihood of the drug treating the disease. A value of 1 indicates that there is a 100% likelihood of the drug treating the disease.

When compared to the known/observed drug-disease association matrix R of FIG. 9, the matrix 1300 of FIG. 13 comprises at least two new drug-disease associations/predictions. In particular, the matrix 1300 shows that drug $d_2$ and disease $s_1$ have an association with a 90% probability that drug $d_2$ can treat disease $s_1$. The matrix 1300 also shows that drug $d_n$, and disease $s_2$ have an association with a 75.2% probability that drug $d_n$, can treat disease $s_1$. FIG. 9 shows that these drug/disease combinations were not previously associated with one another. Stated differently, based on the processes discussed above, the prediction generator 124 determined that drug $d_3$ can potentially be utilized to treat disease $s_1$ and drug $d_n$, can potentially be utilized to treat disease $s_3$ even though these drugs have not been previously used or known to treat these diseases.

Once the prediction generator 124 has calculated $\Theta$, the prediction generator 124 then calculates $\omega$. It should be noted that the process for $\pi$ is similar to $\omega$. Therefore, the following discussion is also applicable to calculating π (where ω is replaced with π, D is replaced with S, and U is replaced with V). In one embodiment, the prediction generator 124 calculates w according to:

$$\min_\omega \sum_{k=1}^{K_d} \omega_k \|D_k - \Sigma\|_F^2 + \delta_1 \|\omega\|_2^2 \text{ subject to } \omega \geq 0, \omega^T 1 = 1 \quad \text{(EQ 14)},$$

where $\Sigma = UU^T$.
Let $$A = [\|D_1 - \Sigma\|_F^2, \|D_2 - \Sigma\|_F^2, \ldots, \|D_{K_d} - \Sigma\|_F^2]^T \quad \text{(EQ 15)}.$$

Then, EQ 17 can be reformulated as:

$$\min_\omega \delta_1 \left\| \omega - \frac{1}{2\delta_1} A \right\|_2^2 + c, \text{ subject to } \omega \geq 0, \omega^T 1 = 1, \quad \text{(EQ 16)}$$

where c is some constant irrelevant to ω. This is a standard Euclidean projection problem and can be efficiently solved using various methods such as that discussed in Chen Y et al. "Projection Onto A Simplex:, arXiv:1101.6081 (2011), which is hereby incorporated by reference in its entirety.

Once ω and π have been calculated the prediction generator 124 calculates the drug-disease cluster relationship matrix Λ according to:

$$\min_\Lambda \|\Theta - U\Lambda V^T\|_F^2, \text{subject to } \Lambda \geq 0 \quad \text{(EQ 17)}.$$

EQ 17 is a non-negative quadratic optimization problem and is solved by the prediction generator 124 utilizing Projected Gradient Descent (PGD). In order to obtain the gradient of the objective of problem (EQ 17) with respect to Λ, it is expanded as:

$$J_\Lambda = \|\Theta - U\Lambda V^T\|_F^2 = tr(\Theta - U\Lambda V^T)^T(\Theta - U\Lambda V^T) = tr(V\Lambda^T U^T U\Lambda V^T) - 2tr(\Theta^T U\Lambda V^T) + c,$$

where c is some constant irrelevant to Λ. Then the prediction generator 124 can derive the gradient $J_\Lambda$ with respect to Λ as $$\frac{\partial J_\Lambda}{\partial \Lambda} = 2U^T U\Lambda V^T V - 2U^T \Theta V. \quad \text{(EQ 18)}$$

In more detail, a non-negative projection operator $P_+(A)$ is introduced as:

$$(P_+(A))_{ij} = \begin{cases} A_{ij} & \text{if } A_{ij} \geq 0 \\ 0 & \text{otherwise} \end{cases}.$$

Then, one Projected Gradient (PG) method that can be performed by the prediction generator 124 for solving the problem $$\min_{A \geq 0} f(A)$$

can be presented as shown in the algorithm 1400 of FIG. 14. FIG. 14 shows that this PG method requires 0<β<1, 0<σ<1, initialization $A^{(0)}$, while ensuring $A^{(0)} \geq 0$. Then, for k=1, 2, . . . , the following calculations are performed:

$$A^{(k)} = P_+(A^{(k-1)} - \alpha_k \nabla f(A^{(k-1)})) \text{ where } \alpha_k = \beta^{t_k}, \text{ and } t_k \text{ is the first nonnegative integer for which}$$

$$f(A^{(k)}) - f(A^{(k-1)}) \leq \sigma \nabla f(A^{(k-1)})^T (A^{(k)} - A^{(k-1)}) \quad \text{(EQ 19)}.$$

Here, the condition in EQ 19 ensures the sufficient decrease of the function value per iteration, and this rule of determining the stepsize is usually referred to as the Armijo rule.

However, the Armijo rule is usually time consuming, thus the prediction generator 124 utilizes the improved PG method shown in the algorithm 1500 of FIG. 15. In particular, this PG method requires 0<β<1, 0<σ<1, Initialization $A^{(0)}$, and $\alpha_0 = 1$ while ensuring $A^{(0)} \geq 0$. The for k=1, 2, . . . , the prediction generator 124 performs the following calculations. First, the prediction generator 124 assigns $\alpha_k = \alpha_{k-1}$. If $\alpha_k$ satisfies the condition in EQ 19, the prediction generator 124 repeatedly increases it by $\alpha_k \leftarrow \alpha_k / \beta$ until either $\alpha_k$ does not satisfy the condition in EQ 19 or $A(\alpha_k/\beta) = A(\alpha_k)$. Otherwise, the prediction generator 124 repeatedly decreases $\alpha_k$ by $\alpha_k \leftarrow \alpha_k \cdot \beta$ until $\alpha_k$ satisfies the condition in EQ 19. The prediction generator 124 sets $A^{(k)} = P_+(A^{(k-1)} - \alpha_k \nabla f(A^{(k-1)}))$.

As a result of the above operations, the prediction generator 124 outputs a resulting drug-disease cluster relationship matrix Λ, which is a latent matrix. FIG. 16 shows one example of this matrix where each row 1602 of the matrix 1600 represents a drug cluster from the drug cluster assignment matrix U and each column 1604 represents a disease cluster from the disease cluster assignment matrix V. Each element 1606 of the matrix 1600 identifies a degree of association between the given drug cluster and the given disease cluster. In the example shown in FIG. 16, drug group $C_{D1}$ has a stronger association (0.5) with $C_{S3}$ than with $C_{S2}$ (0.2).

Once the drug-disease cluster relationship matrix Λ has been generated, the prediction generator 124 calculates the drug and disease cluster assignment matrices U and V. The prediction generator 124 calculates the drug cluster assignment matrix U according to:

$$\min_U \|\Theta - U\Lambda V^T\|_F^2 + \lambda_1 \sum_{k=1}^{K_d} \omega_k \|D_k - UU^T\|_F^2, \text{ subject to } U \geq 0. \quad \text{(EQ 20)}$$

The objective of EQ 20 can be expanded as:

$$J_U = \|\Theta - U\Lambda V^T\|_F^2 + \lambda_1 \sum_{k=1}^{K_d} \omega_k \|D_k - UU^T\|_F^2 = tr(U\Lambda V^T V\Lambda^T U^T) - 2tr(U\Lambda V^T \Theta^T) - 2\lambda_1 tr(U^T \tilde{D} U) + \lambda_1 tr(U^T UU^T U) + c,$$

where $\tilde{D} = \sum_{k=1}^{K_d} \omega_k D_k$ and c is some constant irrelevant to U. Then the gradient of $J_U$ with respect to U is:

$$\frac{\partial J_U}{\partial U} = 2U\Lambda V^T V\Lambda^T - 2\Theta V\Lambda^T - 2\lambda_1 \tilde{D} U + 4\lambda_1 UU^T U. \quad \text{(EQ 21)}$$

The prediction generator 124 calculates the disease cluster assignment matrix V according to:

$$\min_V \|\Theta - U\Lambda V^T\|_F^2 + \lambda_2 \sum_{l=1}^{K_s} \pi_l \|S_l - VV^T\|_F^2, \text{ subject to } V \geq 0. \quad \text{(EQ 22)}$$

Similarly the objective of EQ 22 can be expanded as:

$$J_V = \|\Theta - U\Lambda V^T\|_F^2 + \lambda_2 \sum_{l=1}^{K_s} \pi_l \|S_l - VV^T\|_F^2 = tr(V\Lambda^T U^T U\Lambda V^T) -$$

$$2tr(V^T \Theta^T U\Lambda) - 2\lambda_2 tr(V^T \tilde{S} V) + \lambda_2 tr(V^T VV^T V) + c,$$

where $\tilde{S} = \sum_{l=1}^{K_s} \pi_l S_l$ and c is some constant irrelevant to V. Then the gradient of $J_V$ with respect to V is:

$$\frac{\partial J_V}{\partial V} = 2V\Lambda^T U^T U\Lambda - 2\Theta^T U\Lambda - 2\lambda_2 \tilde{S} V + 4\lambda_2 VV^T V. \quad (EQ\ 23)$$

The prediction generator 124 then outputs U and V matrices similar to those shown in FIGS. 11 and 12.

Once the prediction generator 124 has calculated $\Lambda$, $\Theta$, $\omega$, $\pi$, U, and V it calculates $J_0$ (the reconstruction loss of observed drug-disease associations) according to EQ 8, $J_1$ (the reconstruction loss of drug similarities) according to EQ 9, and $J_2$ (the reconstruction loss of disease similarities) according to EQ 10 to determine if a convergence has occurred. If so, the prediction generator 124 outputs the optimized $\Theta$, $\omega$, $\pi$, U, and V. If convergence has not occurred, the prediction generator 124 performs another iteration of the process shown in FIG. 10 using the values for $\Lambda$, $\Theta$, $\omega$, $\pi$, U, and V calculated in the previous iteration. This process continues until convergence is reached.

The computational cost involved in each BCD iteration includes the following. When updating $\Theta$, the main computation happens at calculating $U\Lambda V^T$, which takes $O(nK_d K_s + nmK_s)$ time. When updating $\omega$, the main computation happens at calculating $UU^T$, which takes $O(n^2 K_d)$ time. The Euclidean projection takes $O(K_d \log K_d)$ time. When updating, the main computation happens at calculating $VV^T$, which takes $O(m^2 K_s)$ time. The Euclidean projection takes $O(K_s \log K_s)$ time. Updating $\Lambda$ involves PGD iterations. We just need to evaluate $U^T \Theta V$ once, which takes $O(K_d nm + K_d K_s m)$ time. At each iteration evaluating $U^T U\Lambda V^T V$ takes $O(K_d{}^2 K_s + K_s{}^2 K_d)$ time (as $UU^T$ and $VV^T$ are already computed), and evaluating the $J_\Lambda$ takes $O(K_d{}^2 K_d)$ time. Updating U involves PGD iterations. $\Theta V\Lambda^T$ and $\Lambda V^T V\Lambda^T$ only need to be evaluated once, which takes $O(nK_d K_s)$ and $O(K_d K_s{}^2 + K_s K_d{}^2)$ time. At each iteration evaluating $U\Lambda V^T V\Lambda^T$ takes $O(nK_d{}^2)$ time, $\tilde{D} U$ takes $O(n^2 K_d)$, $UU^T U$ takes $O(nK_d{}^2 + n^2 K_d)$ time, and evaluating $J_U$ takes $O(nK_d{}^2)$ time. Updating V involves PGD iterations. $\Lambda^T U^T U\Lambda$ and $\Theta^T U\Lambda$ only need to be evaluated once once, which takes $O(nK_d K_s + nK_d{}^2)$ and $O(mnK_d + mK_d K_s)$ time. At each iteration evaluating $V\Lambda^T U^T U\Lambda$ takes $O(mK_s{}^2)$ time, $\tilde{S}V$ takes $O(m^2 K_s)$ time, $VV^T V$ takes $O(mK_s{}^2 + K_s m^2)$ time, and evaluating $J_V$ takes $O(mK_s{}^2)$ time. Adding up everything together, and considering the fact that $\max(K_d, K_s) \ll \min(m, n)$, the rough computational complexity is $O(R\tilde{r}mn)$, where R is the number of BCD iterations, and $\tilde{r}$ is the average PGD iterations when updating $\Lambda$, U, and V.

Figure 17:
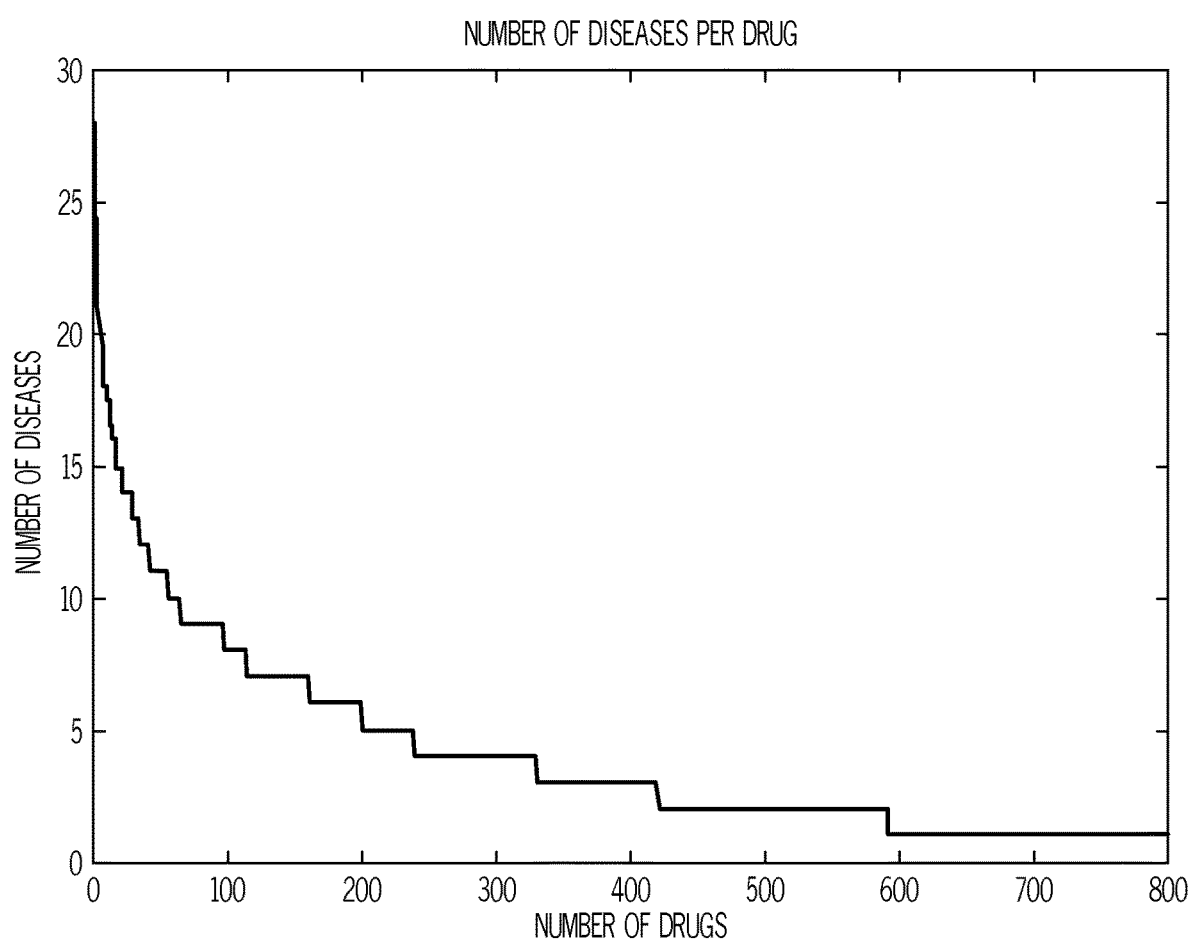
FIG. 17 is a graph showing the number of indicated diseases per drug according to one embodiment of the present disclosure.
Figure 18:
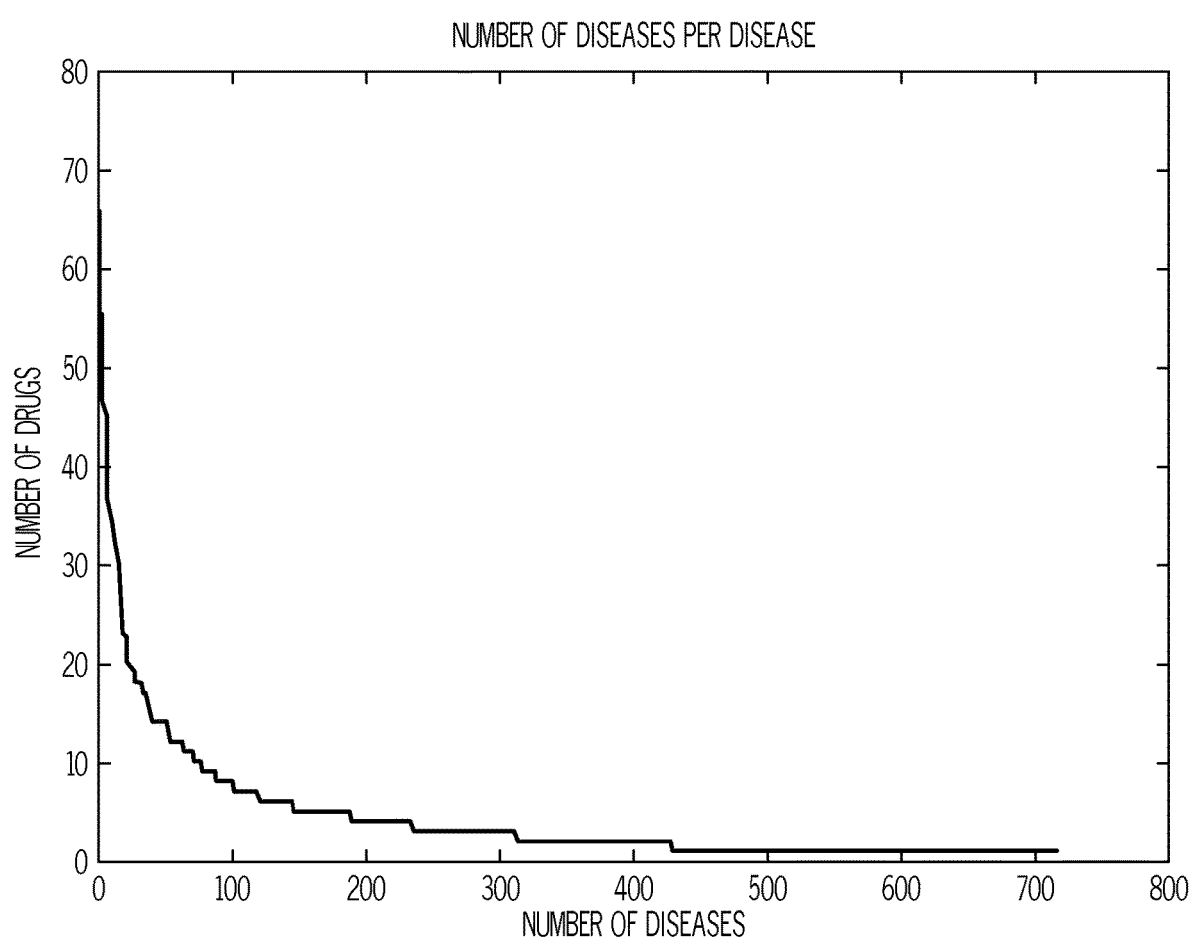
FIG. 18 is a graph showing the number of drugs per disease according to one embodiment of the present disclosure.

The following discussion presents various experimental results of various DDR methods performed by the prediction generator 124 on a drug repositioning task. In one experiment performed by the inventors, a benchmark dataset was used to test the performance of the prediction generator 124 using a community standard. This dataset was extracted from the National Drug File-Reference Terminology (NDF-RT) produced by the U.S. Department of Veterans Affairs, Veterans Health Administration (VHA). The dataset spanned 3,250 treatment associations between 799 drugs and 719 diseases. Drug information was considered from three data sources: chemical structure, target protein, and side effect. Thus, three 799×799 matrices were used to represent drug similarities between 799 drugs from different perspectives. Similarly, disease information was considered from three data sources: disease phenotype, disease ontology, and disease gene. Thus, three 719×719 matrices were used to represent disease similarities between 719 human diseases from different perspectives. The presence or absence of known associations between drugs and diseases was denoted by 1 or 0 respectively. Thus, a 799×719 matrix R was used to represent the known drug-disease associations. The statistics of the known drug-disease associations from known drug-disease association data is plotted in FIGS. 17 and 18. In that dataset, most of the drugs (75%) treat <5 diseases; 18% of drugs treat 5 to 10 diseases; and only 7% of drugs treat >10 diseases (FIGS. 17 and 18). Although the disease hypertension has 78 related drugs, 80% of diseases have only <5 drugs; 10% of diseases have 5-10 drugs; and the remaining 10% of diseases have >10 drugs.

A 10-fold cross-validation scheme was used to evaluate drug repositioning approaches. To ensure the validity of the test cases, all the associations involved with 10% of the drugs in each fold were held out, rather than holding out associations directly. To obtain robust results, 50 independent cross-validation runs were performed, in each of which a different random partition of dataset to 10 parts was used. In the comparisons, five drug repositioning methods were considered. The first method was the DDR method of one or more embodiments using Simple Average. This method only considers reconstruction loss of observed drug-disease associations (i.e., $J_0$ of objective formula (EQ 7), and assumes each drug/disease source was equally informative. Thus, this method uses the average of drug/disease similarity matrices as the integrated drug/disease similarity.

The send method was the DDR method of one or more embodiments with Weighted Drug Similarity. This method considers reconstruction losses of observed drug-disease associations and drug similarities (i.e., $J_0$ and $J_1$ in objective formula (EQ 7)). This method uses the average of disease similarity matrices as integrated disease similarity, and automatically learns drug similarity weight vector ($\omega$) based on the contributions of drug information sources to the prediction. The third method was the DDR method of one or more embodiments with Weighted Disease Similarity. This method considers reconstruction losses of observed drug-disease associations and disease similarities (i.e., $J_0$ and $J_2$ in objective formula (EQ 7)). This method uses the average of drug similarity matrices as integrated drug similarity, and automatically learns disease similarity weight vector ($\pi$) based on the contributions of disease information sources to the prediction.

Figure 19:
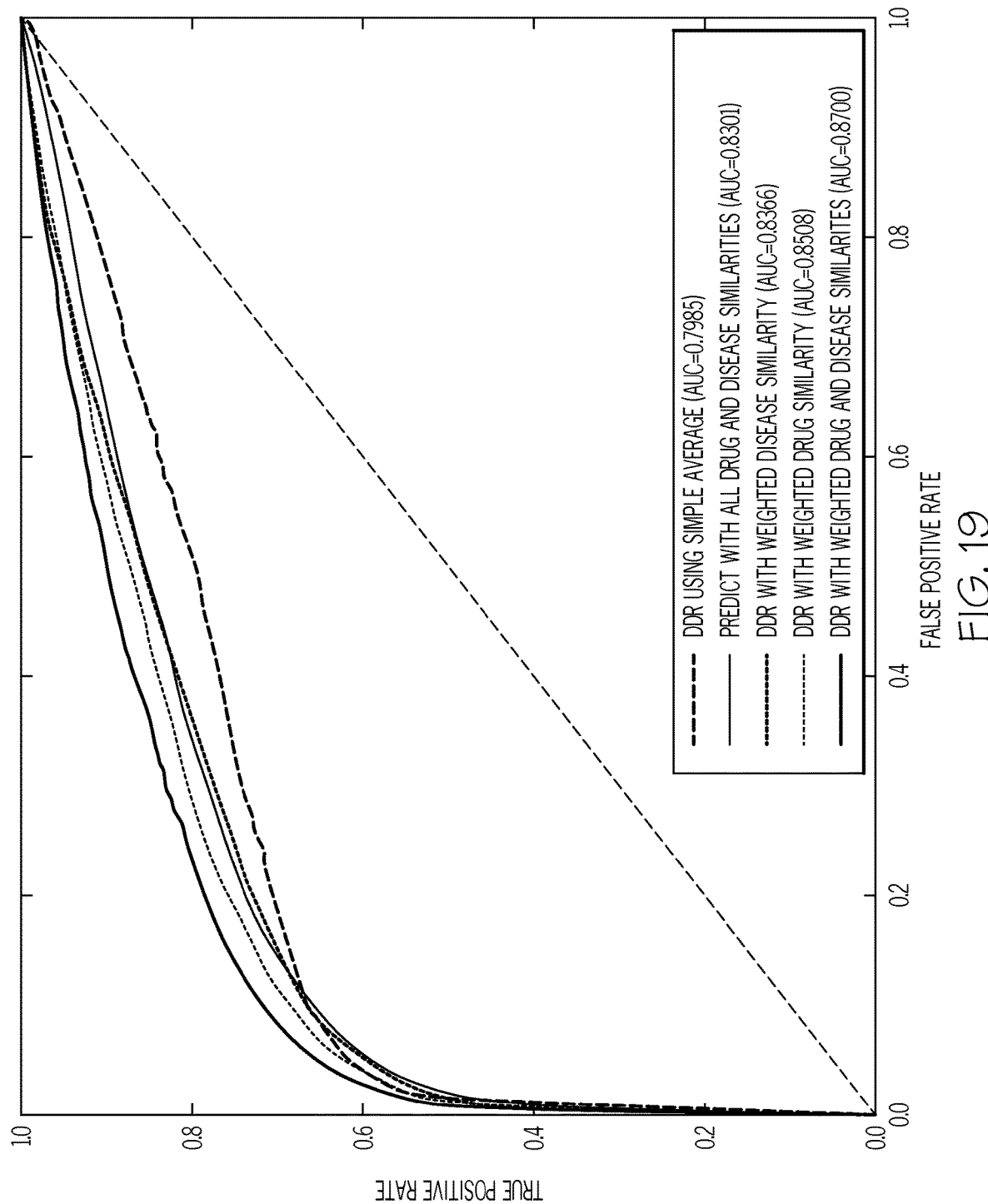
FIG. 19 is a graph showing averaged ROC comparison of five drug repositioning approaches generated from 50 runs of 10-fold cross-validation.

The fourth method was the DDR method of one or more embodiments with Weighted Drug and Disease Similarities. This method considers all reconstruction losses proposed in the paper (i.e., formula (EQ 7) as a whole). This method automatically learns drug similarity weight vector ($\omega$) and disease similarity weight vector ($\pi$) together based on the contributions of drug and disease information sources to the prediction. The fifth method was PREDICT, which uses un-weighted geometric mean of pairs of drug-drug and disease-disease similarity measures to construct classification features and subsequently learns a logistic regression classifier that distinguishes between true and false drug-disease associations. PREDICT could not provide weight for each drug/disease information source. The PREDICT method is further discussed in Gottlieb et al., "PREDICT: A Method For Inferring Novel Drug Indications With Application To Personalized Medicine". Mol Syst Biol 2011; 7:496. FIG. 19 shows the averaged ROC curves of 50 runs of the cross-validation for different methods based on the experiment.

FIG. 19 shows that the DDR framework of one or more embodiments is effective for drug repositioning tasks. Without considering reconstruction loss of any similarity measure, DDR using Simple Average obtains an averaged AUC score of 0.7985. When considering weighted drug similarity (i.e., reconstruction loss of drug similarities) or weighted disease similarity (i.e., reconstruction loss of disease similarities), DDRs obtain averaged AUC scores of 0.8508 or 0.8366 respectively. In the experiment, drug-based optimization (i.e., DDR with Weighted Drug Similarity) obtains a higher AUC score than disease-based optimization (i.e., DDR with Weighted Disease Similarity). This could be partially explained with the following reason. The 799 drugs that were studied are marketed medications, which usually have rich and precise pharmacological data; thus drug-based optimization might be preferred in this case. For novel drugs or clinical candidates, disease-based optimization might be preferred to overcome missing knowledge in the pharmacology of a drug (e.g., additional targets, unknown side effect). When considering weighted drug similarity and weighted disease similarity together, DDR obtain the highest averaged AUC score (0.8700). The observation indicates that drug-based optimization and disease-based optimization could be complementary, and computational drug repositioning tasks should optimize both drug similarity and disease similarity. Another observation is PREDICT with All Drug and Disease Similarities is less accurate than DDR.

Figure 20:
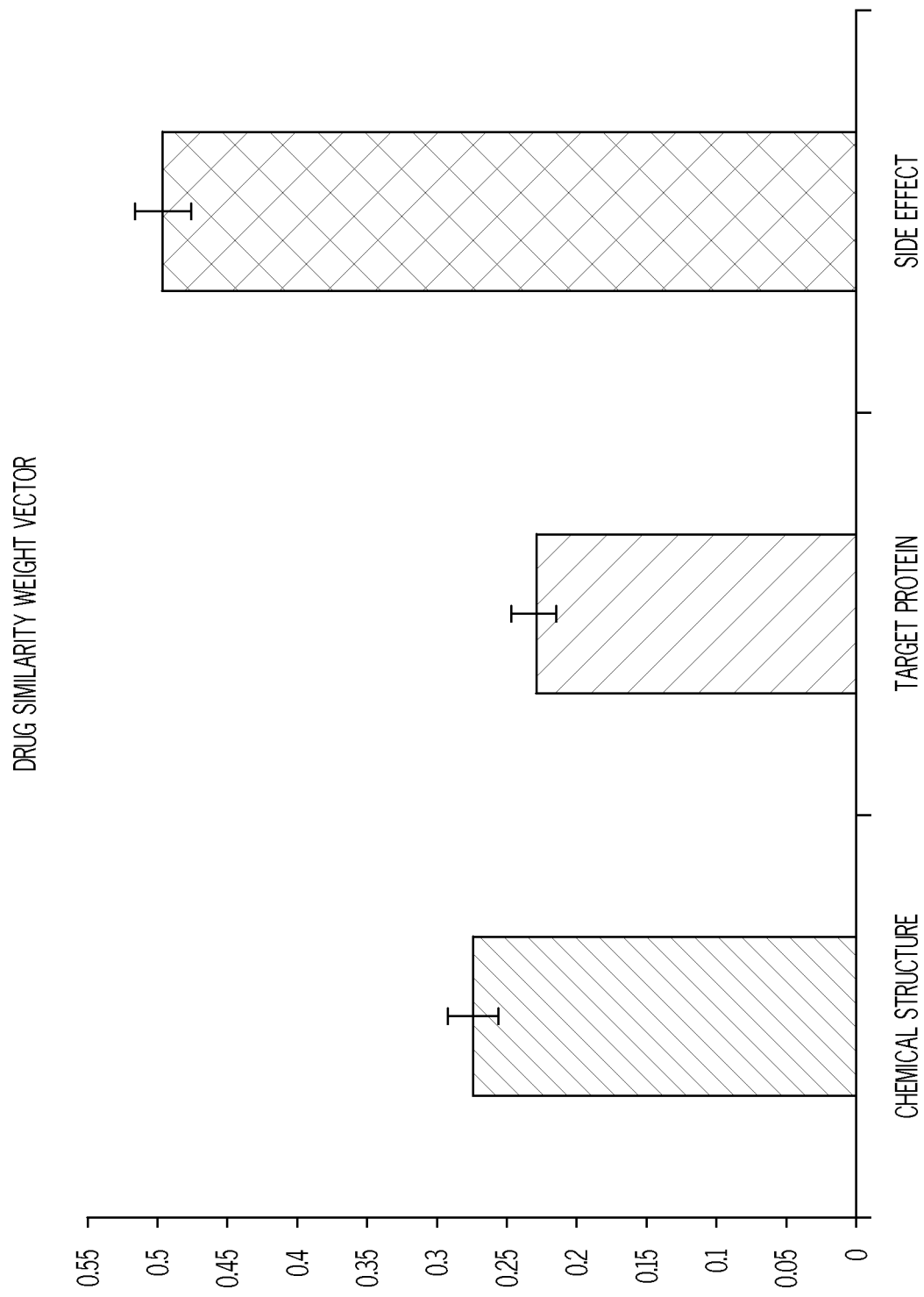
FIG. 20 is a graph showing the weights for various drug similarity sources according to one embodiment of the present disclosure.
Figure 21:
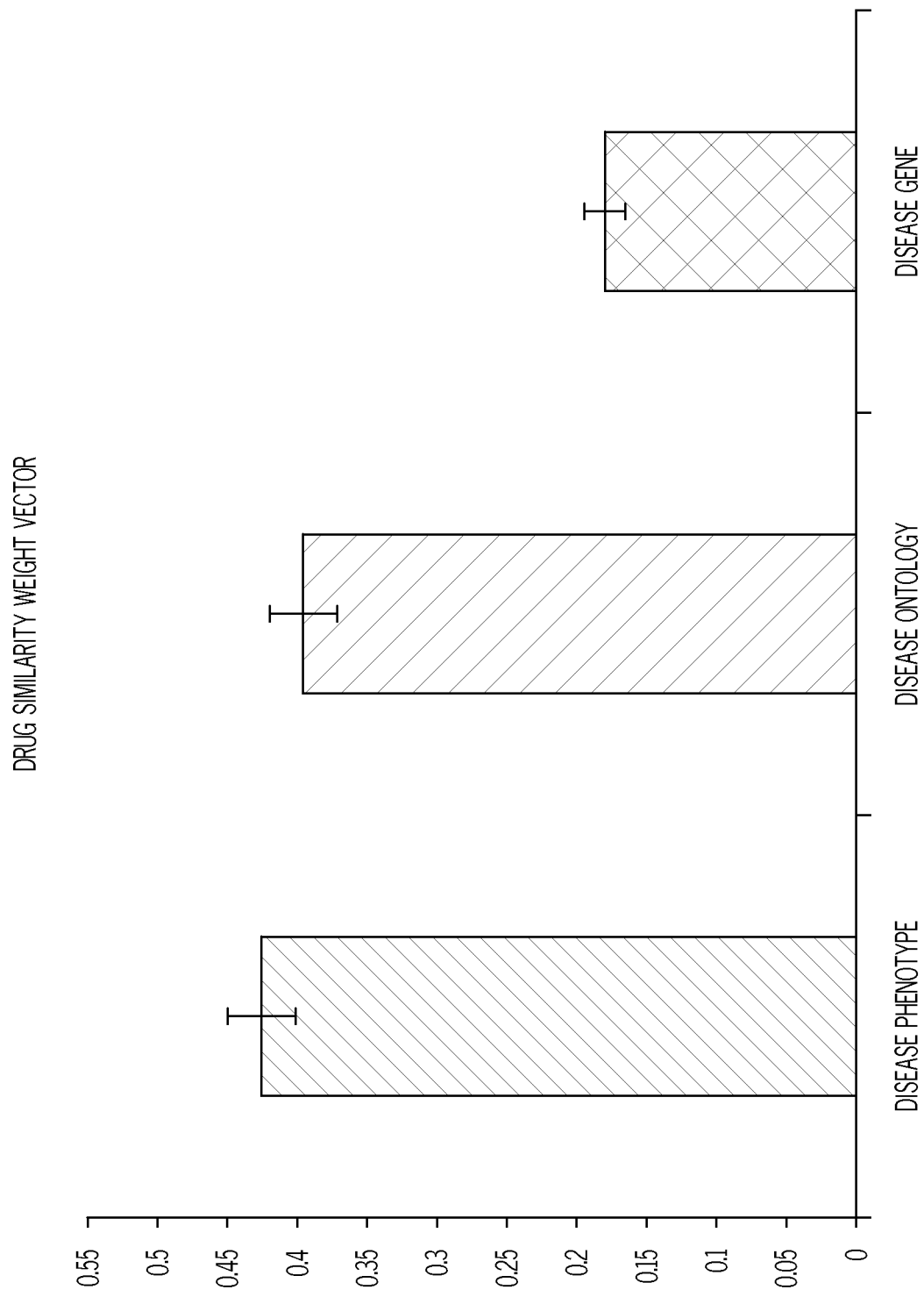
FIG. 21 is a graph showing the weights for various disease similarity sources according to one embodiment of the present disclosure.

One advantageous characteristic of the DDR method performed by the prediction generator 124 is that it provides interpretable importance of different information sources based on their contributions to the prediction. The i-th element of drug/disease weight vector $\omega/\pi$ corresponds to the i-th drug/disease data sources. Since $\omega/\pi$ was constrained to be in a simplex in problem formula (EQ 11), the sum of all elements of $\omega/\pi$ is 1. Obtained from DDR with Weighted Drug and Disease Similarities, the averaged DDR weights of each data source and their standard deviations during the cross-validation experiments are plotted in FIGS. 20 and 21. For drug data sources, chemical structure obtains averaged weight of 0.2744, target protein obtains averaged weight of 0.2295, and side effect obtains a much higher averaged weight of 0.4961 (FIG. 20). This can be partially explained with the following reasons. Chemical structure and target protein sources focus on drug's molecular mechanism of action (MOA) from a genotypic perspective. However, the pre-clinical outcomes based on MOA often do not correlate well with therapeutic efficacy in drug development. It is estimated that of all compounds effective in cell assays, only 30% of them could work in animals. Even worse, only 5% of them could work in humans. Side effects are generated when drugs bind to off-targets, which perturb unexpected metabolic or signaling pathways. For marketed drugs, which have relatively complete side effect profiles, side effect information from clinical patients may be seen as valuable read-outs of drug effects directly on human bodies (i.e., with less translational problems). Thus, side effects could serve as a promising perspective for drug repositioning. For disease data sources, phenotype obtains averaged weight of 0.4248, disease ontology obtains averaged weight of 0.3958, and disease gene obtains a lower averaged weight of 0.1794 (FIG. 21). The lower weight of disease gene data source may be due to the fact that the gap between phenotype (human disease) and genotype (human gene) is too large, and the known associations between diseases and genes (obtained from OMIM) are incomplete.

The inventors also performed an additional leave-disease-out experiment to demonstrate the capability of DDR of one or more embodiments on uncovering drug-disease associations and predicting novel drug candidates for each disease. To ensure the validity of the test cases, all the known drug-disease associations were held out with the tested disease. The validation setting mimics a real-world setting: once rare/unknown diseases without any treatment information arise, a computational drug repositioning method should provide potential drugs based on characteristics (e.g. phenotypes, related genes) of the new diseases and the existing drug/disease similarities. In the experiment, each disease i was alternatively left out and the DDR (considered weighted drug and disease similarities) process was performed by the prediction generator 124. More specifically, all elements in the i-th column of matrix R were set to 0. This R was used along with drug/disease similarity matrices as inputs of to the prediction generator 124. Then, the i-th column of the densified estimated matrix $\Theta$ was used as the drug prediction scores for the disease i. In this way, prediction scores were obtained for all possible associations between the 799 drugs and 719 diseases.

As an example, treatment predictions for Alzheimer's disease (AD) were analyzed. For the six drugs which are known to treat AD, the prediction generator 124 assigned scores of 0.7091 to Selegiline, 0.6745 to Valproic Acid, 0.6348 to Galantamine, 0.5675 to Donepezil, 0.5571 to Tacrine, and 0.5233 to Rivastigmine, which are significantly larger than those of the other 793 drugs (mean and standard deviation are 0.1565±0.1628). FIG. 22 shows the top 10 drugs predicted for AD by the prediction generator 124, where an "*" denotes that the drug is known and approved to treat the disease. Of the 10 drugs, only three (Selegiline, Valproic Acid, and Galantamine) appear in the known drug-disease association list. The remaining 7 predicted drugs (along with other high-ranked ones in the leave-disease-out experiment) can be considered as drug repositioning candidates for AD. Some predictions are explainable and supported by clinical evidence from ClinicalTrials.gov (i.e., pharmaceutical investigators have been aware of the associations, which are still in the experimental stages).

Figure 23:
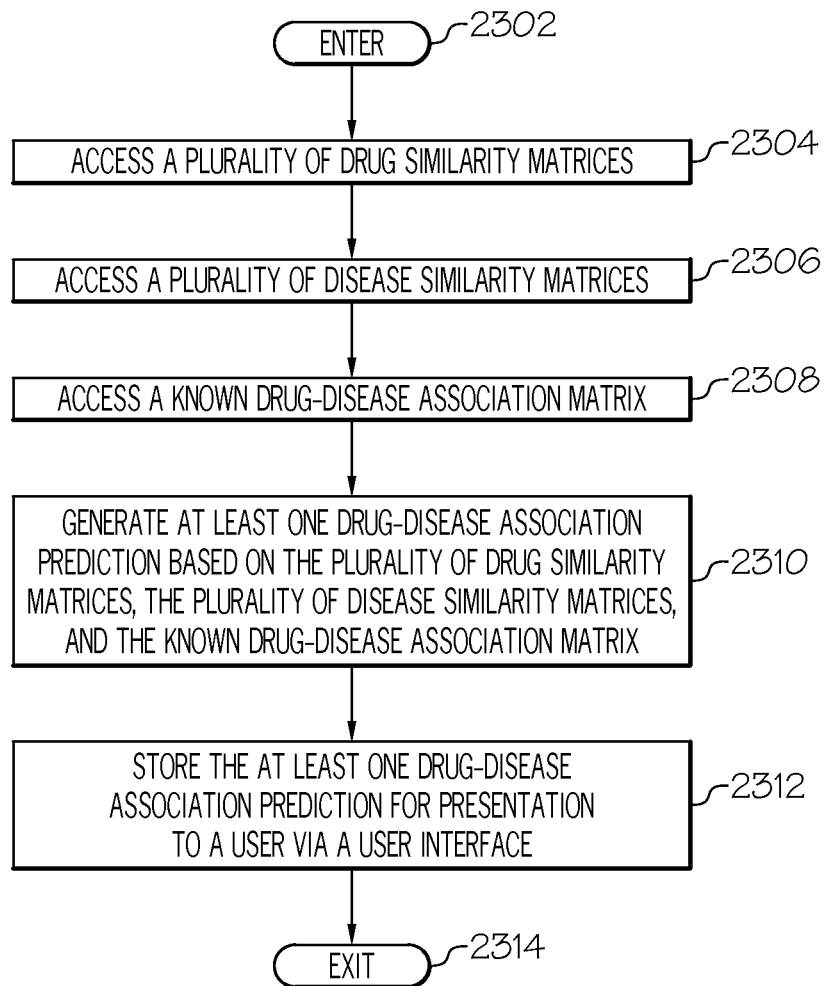
FIG. 23 is an operational flow diagram illustrating one example of a process for performing a drug repositioning task according to one embodiment of the present disclosure.

FIG. 23 is an operational flow diagrams illustrating one example of a process for predicting drug-disease associations. The operational flow diagram of FIG. 23 beings at step 2302 and flows directly to step 2304. The drug repositioning manger 118, at step 2304, accesses a plurality of drug similarity matrices. Each of the plurality of drug similarity matrices is associated with a different drug information source. The drug repositioning manger 118, at step 2306, accesses a plurality of disease similarity matrices. Each of the plurality of disease similarity matrices is associated with a different disease information source. The drug repositioning manger 118, at step 2308, also accesses a known drug-disease association matrix. The known drug-disease association matrix indicating if a given drug identified is known to treat a given disease.

The drug repositioning manger 118, at step 2310, generates at least one drug-disease association prediction based on the plurality of drug similarity matrices, the plurality of disease similarity matrices, and the known drug-disease association matrix. The at least one drug-disease association prediction identifying a previously unknown association between a given drug and a given disease, and a probability that the given disease is treatable by the given drug. The drug repositioning manger 118, at step 2312, stores the at least one drug-disease association prediction for presentation to a user via a user interface. The control flow exits at step 2314.

Figure 24:
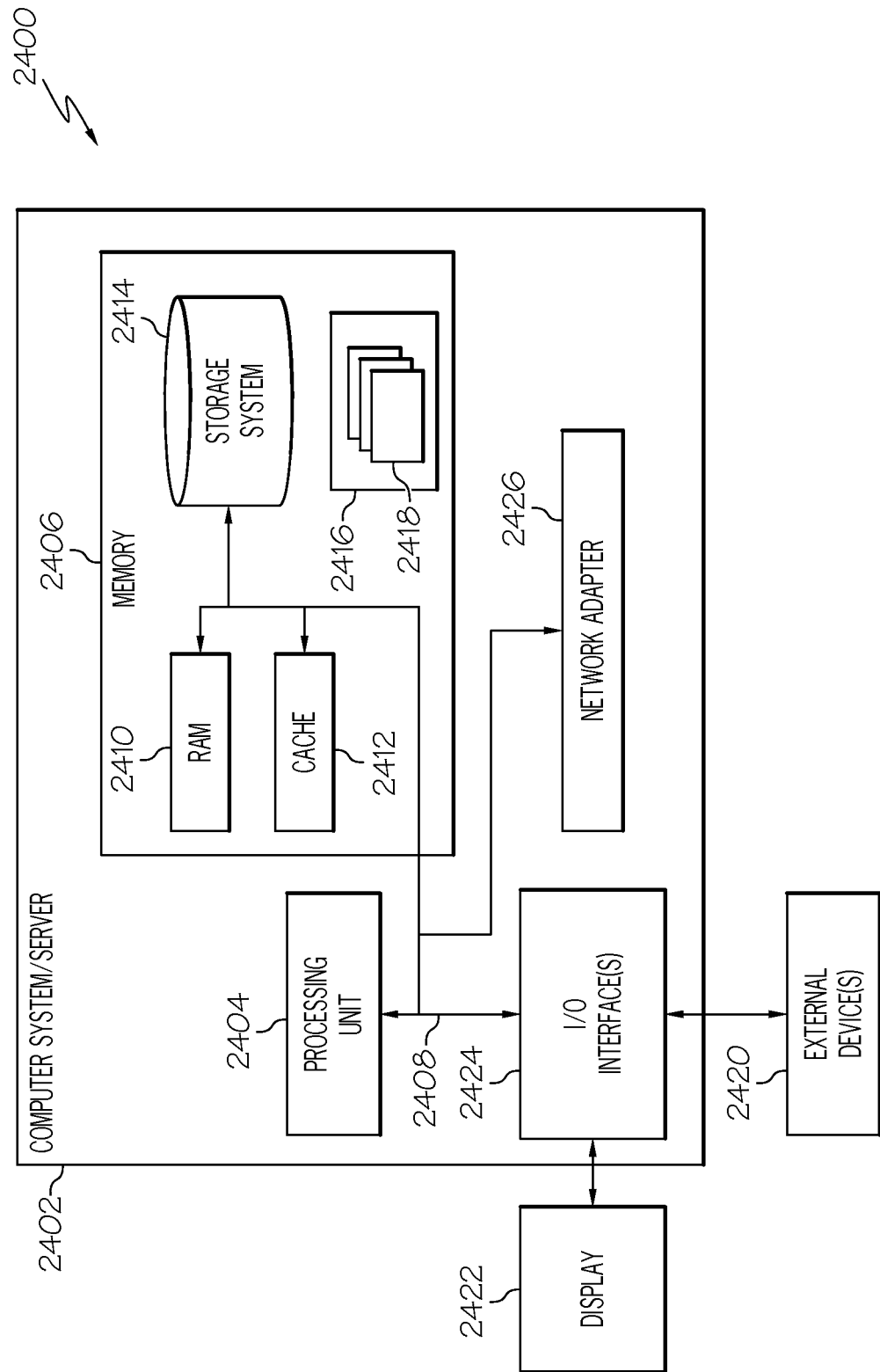
FIG. 24 is a block diagram illustrating one example of an information processing system according to one embodiment of the present disclosure.

Referring now to FIG. 24, this figure is a block diagram illustrating an information processing system that can be utilized in various embodiments of the present disclosure. The information processing system 2402 is based upon a suitably configured processing system configured to implement one or more embodiments of the present disclosure. Any suitably configured processing system can be used as the information processing system 2402 in embodiments of the present disclosure. In another embodiment, the information processing system 2402 is a special purpose information processing system configured to perform one or more embodiments discussed above. The components of the information processing system 2402 can include, but are not limited to, one or more processors or processing units 2404, a system memory 2406, and a bus 2408 that couples various system components including the system memory 2406 to the processor 2404.

The bus 2408 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Although not shown in FIG. 24, the main memory 2406 includes at least the drug repositioning manager 118 and its components discussed above with respect to FIG. 1. Each of these components can reside within the processor 2404, or be a separate hardware component. The system memory 2406 can also include computer system readable media in the form of volatile memory, such as random access memory (RAM) 2410 and/or cache memory 2412. The information processing system 2402 can further include other removable/non-removable, volatile/non-volatile computer system storage media. By way of example only, a storage system 2414 can be provided for reading from and writing to a non-removable or removable, non-volatile media such as one or more solid state disks and/or magnetic media (typically called a "hard drive"). A magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus 2408 by one or more data media interfaces. The memory 2406 can include at least one program product having a set of program modules that are configured to carry out the functions of an embodiment of the present disclosure.

Program/utility 2416, having a set of program modules 2418, may be stored in memory 2406 by way of example, and not limitation, as well as an operating system, one or more application programs, other program modules, and program data. Each of the operating system, one or more application programs, other program modules, and program data or some combination thereof, may include an implementation of a networking environment. Program modules 2418 generally carry out the functions and/or methodologies of embodiments of the present disclosure.

The information processing system 2402 can also communicate with one or more external devices 2420 such as a keyboard, a pointing device, a display 2422, etc.; one or more devices that enable a user to interact with the information processing system 2402; and/or any devices (e.g., network card, modem, etc.) that enable computer system/server 2402 to communicate with one or more other computing devices. Such communication can occur via I/O interfaces 2424. Still yet, the information processing system 2402 can communicate with one or more networks such as a local area network (LAN), a general wide area network (WAN), and/or a public network (e.g., the Internet) via network adapter 2426. As depicted, the network adapter 2426 communicates with the other components of information processing system 2402 via the bus 2408. Other hardware and/or software components can also be used in conjunction with the information processing system 2402. Examples include, but are not limited to: microcode, device drivers, redundant processing units, external disk drive arrays, RAID systems, tape drives, and data archival storage systems.

As will be appreciated by one skilled in the art, aspects of the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically ended device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source de or object de written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of identifying patterns for drug-disease associations and treating diseases based thereon, the method comprising:
    executing an algorithm that programs a drug repositioning manager coupled to one or more processors of at least one information processing to perform training operations comprising
        accessing a plurality of drug similarity matrices, wherein each of the plurality of drug similarity matrices is associated with a different drug information source, wherein each different drug information source provides a different set of drug data utilized to generate the drug similarity matrix associated therewith;
        accessing a plurality of disease similarity matrices, wherein each of the plurality of disease similarity matrices is associated with a different disease information source, wherein each different disease information source provides a different set of disease data utilized to generate the disease similarity matrix associated therewith;
        accessing a known drug-disease association matrix, the known drug-disease association matrix indicating if a drug identified in the known drug-disease association matrix is known to treat a disease identified in the known drug-disease association matrix; and generating at least one drug-disease association prediction using an optimization model with a plurality of input training variables including n the plurality of drug similarity matrices, the plurality of disease similarity matrices, and the known drug-disease association matrix, a densified estimation of observer drug-disease association matrix, drug similarity weight vector, and disease similarity weight vector, the at least one drug-disease association prediction identifying a previously unknown association between a given drug and a given disease, and a probability that the given disease is treatable by the given drug and the optimization model produces reconstruction losses due to outputs that overfit the plurality of input training variables;

performing each of
   a) solving the optimization algorithm using sets from the plurality of input training variables through a gradient descent analytical process to identify a local minimum of a differentiable function;
   b) determining if the reconstruction loses are decreasing; and
   c) in response to reconstruction losses decreasing repeating steps a thru step c; and
selecting the given drug over another drug and utilized to treat one or more diseases based on the at least one drug-disease association prediction.

2. The method of claim 1, wherein accessing a plurality of drug similarity matrices comprises:
   receiving a plurality of drug datasets associated with a plurality of drugs, each of the plurality of drug datasets being received from a different drug information source, and each of the plurality of drug datasets comprising data associated with one or more attributes of each of the plurality of drugs;
   calculating a plurality of similarity measures between each pair of drugs in the plurality of drugs, where each of the plurality of similarity measures is calculated based on a different one of the plurality of drug datasets; and
   generating the plurality of drug similarity matrices based on the plurality of similarity measures, where each of the plurality of drug similarity matrices comprises a different one of the plurality of similarity measures.

3. The method of claim 1, wherein accessing a plurality of disease similarity matrices comprises:
   receiving a plurality of disease datasets associated with a plurality of diseases, each of the plurality of disease datasets being received from a different disease information source, and each of the plurality of disease datasets comprising data associated with one or more attributes of each of the plurality of diseases;
   calculating a plurality of similarity measures between each pair of diseases in the plurality of diseases, where each of the plurality of similarity measures is calculated based on a different one of the plurality of drug disease; and
   generating the plurality of disease similarity matrices based on the plurality of similarity measures, where each of the plurality of disease similarity matrices comprises a different one of the plurality of similarity measures.

4. The method of claim 2, wherein at least a first of the plurality of drug datasets comprises drug chemical structure data for each of the plurality of drugs, where at least a send of the plurality of drug datasets comprises drug target protein data for each of the plurality of drugs, and where at least a third of the plurality of drug datasets comprises drug side effect data for each of the plurality of drugs.

5. The method of claim 3, wherein at least a first of the plurality of disease datasets comprises disease phenotype data for each of the plurality of diseases, where at least a second of the plurality of diseases datasets comprises disease ontology data for each of the plurality of diseases, and where at least a third of the plurality of diseases datasets comprises disease gene data for each of the plurality of drugs.

6. The method of claim 1, wherein generating the at least one drug-disease association prediction comprises:
   analyzing the plurality of drug similarity matrices, the plurality of disease similarity matrices, and the known drug-disease association matrix by minimizing an objective defined as:

$$J = J_0 + \lambda_1 J_1 + \lambda_2 J_2,$$

where $J_0$ is a reconstruction loss of observed drug-disease associations defined as:
   $J_0 = \|\Theta - U\Lambda V^T\|_F^2$, where $\Theta$ is an estimated drug-disease association matrix comprising the at least one drug-disease association prediction, U is a drug cluster assignment matrix, $\Lambda$ is a drug-disease cluster relationship matrix, V is a disease cluster assignment matrix, T indicates a transpose, and $\|\cdot\|_F$ denotes Frobenius norm of a matrix,
   where $J_1$ is a reconstruction loss of drug similarities defined as:
   $J_1 = \Sigma_{k=1}^{K_d} \omega_k \|D_k - UU^T\|_F^2 + \delta_1 \|\omega\|_2^2$, where $K_d$ is a plurality of drug information sources associated with the plurality of drug similarity matrices, $\omega$ is an importance factor assigned to a given drug information source in the plurality of drug information sources, $D_k$ is one of the plurality of drug similarity matrices, and $\delta$ is a tradeoff parameter,
   $J_2$ is a reconstruction loss of drug similarities defined as:
   $J_2 = \Sigma_{l=1}^{K_s} \pi_l \|S_l - VV^T\|_F^2 + \delta_2 \|\pi\|_2^2$, where $K_s$ is a plurality of disease information sources associated with the plurality of disease similarity matrices, $\pi$ is an importance factor assigned to a given disease information source in the plurality of disease information sources, and $S_l$ is one of the plurality of disease similarity matrices, and $\delta$ is a tradeoff parameter, and
   where $\lambda$ is a user-defined weight.

7. The method of claim 6, wherein generating the at least one drug-disease association prediction further comprises:
   iteratively calculating the estimated drug-disease association matrix $\Theta$, each drug information source importance factor, each disease information source importance factor $\pi$, the drug-disease cluster relationship matrix $\Lambda$, the drug cluster assignment matrix U, and the disease cluster assignment matrix V until the objective is minimized.

8. The method of claim 7, where at a first iteration $\omega$ is initialized as $\omega = (1/K_d)1 \in R^K$, $\pi$ is initialized as $\pi = (1/K_s)1 \in R^{K_s \times 1}$, $\Lambda$ is initialized with random values, U is initialized by performing Symmetric Nonnegative Matrix Factorization on $\tilde{D} = \Sigma_{k=1}^{K_d} \omega_k D_k$, and V is initialized by performing Symmetric Nonnegative Matrix Factorization on $\tilde{S} = \Sigma_{l=1}^{K_s} \pi_l S_l$.

9. The method of claim 8, wherein at each iteration:
   the estimated drug-disease association matrix $\Theta$ is calculated according to:
   $\min_\Theta \|\Theta - W\|_F^2$, subject to $P_\Omega(\Theta) = P_\Omega(R)$, where $W = U\Lambda V^T$, $\Theta$ is a set of indices of observed associations in R, and $P_\Theta$ is a projection operator on obtaining entries of a matrix indexed by the indices in $\Theta$, the drug information source importance factor $\pi$ is calculated according to:

$\min_\pi \sum_{k=1}^{K_d} \omega_k \|D_k - \Sigma\|_F^2 + \delta_1 \|\omega\|_2^2$, subject to $\omega \geq 0$, $\omega^T 1 = 1$, where $\Sigma = UU^T$ the disease information source importance factor $\pi$ calculated according to:

$\min_\pi \sum_{k=1}^{K_s} \pi_l \|S_l - \Sigma\|_F^2 + \delta_1 \|\pi\|_2^2$, subject to $\pi \geq 0$, $\pi^T 1 = 1$, where $\Sigma = VV^T$, and the drug-disease cluster relationship matrix $\Lambda$ is calculated according to:

$\min_\Lambda \|\Theta - U\Lambda V^T\|_F^2$, subject to $\Lambda \geq 0$.

10. The method of claim 9, wherein at each iteration:

the drug cluster assignment matrix U is calculated according to:

$$\min_U \|\Theta - U\Lambda V^T\|_F^2 + \lambda_1 \sum_{k=1}^{K_d} \omega_k \|D_k - UU^T\|_F^2,$$

subject to $U \geq 0$, and the disease cluster assignment matrix V is calculated according to:

$$\min_V \|\Theta - U\Lambda V^T\|_F^2 + \lambda_2 \sum_{l=1}^{K_s} \pi_l \|S_l - VV^T\|_F^2,$$

subject to $U \geq 0$.

11. The method of claim 1, wherein generating the least one drug-disease association prediction further comprises outputting a weight of each different drug information source based on a contribution of the drug information source to the at least one drug-disease association prediction, wherein the weight of each different drug information source provides a quantifiable importance of the different drug information source with respect to the least one drug-disease association prediction, and outputting a weight of each different disease information source based on a contribution of the disease information source to the at least one drug-disease association prediction, wherein the weight of each different disease information source provides a quantifiable importance of the different disease information source with respect to the least one drug-disease association prediction, wherein the at least one drug-disease association prediction is generated based, in part, on the weight of each different drug information source and the weight of each different disease information source, and wherein the given drug is selected over another drug and utilized to treat one or more diseases based on the at least one drug-disease association prediction.

* * * * *